US011457800B2

(12) United States Patent
Yamamoto

(10) Patent No.: US 11,457,800 B2
(45) Date of Patent: Oct. 4, 2022

(54) ENDOSCOPE DEVICE

(71) Applicant: OLYMPUS CORPORATION, Hachioji (JP)

(72) Inventor: Yusuke Yamamoto, Kawasaki (JP)

(73) Assignee: OLYMPUS CORPORATION, Tokyo (JP)

(*) Notice: Subject to any disclaimer, the term of this patent is extended or adjusted under 35 U.S.C. 154(b) by 306 days.

(21) Appl. No.: 16/698,222

(22) Filed: Nov. 27, 2019

(65) Prior Publication Data

US 2020/0093358 A1 Mar. 26, 2020

Related U.S. Application Data

(63) Continuation of application No. PCT/JP2017/020796, filed on Jun. 5, 2017.

(51) Int. Cl.
*A61B 1/04* (2006.01)
*A61B 1/00* (2006.01)
(Continued)

(52) U.S. Cl.
CPC .......... *A61B 1/043* (2013.01); *A61B 1/00009* (2013.01); *A61B 1/051* (2013.01);
(Continued)

(58) Field of Classification Search
CPC ..... A61B 1/043; A61B 1/0646; A61B 1/0638; A61B 1/051; A61B 1/00009
See application file for complete search history.

(56) References Cited

U.S. PATENT DOCUMENTS 9,271,635 B2 * 3/2016 Watanabe ............... A61B 1/043
10,779,734 B2 * 9/2020 Fengler .................. A61B 1/043
(Continued)

FOREIGN PATENT DOCUMENTS

JP 2005-319115 A 11/2005
JP 2006-296635 A 11/2006
(Continued)

OTHER PUBLICATIONS

International Search Report dated Aug. 22, 2017, issued in counterpart International Application No. PCT/JP2017/020796, with English translation (4 pages).

*Primary Examiner* — John P Leubecker
*Assistant Examiner* — Jae Woo
(74) *Attorney, Agent, or Firm* — WHDA, LLP

(57) ABSTRACT

In an endoscope device, a light source unit is configured to sequentially emit first illumination light and second illumination light. The first illumination light includes visible light. The second illumination light includes first excitation light. At least the second illumination light out of the first illumination light and the second illumination light includes second excitation light. An excitation wavelength blocking filter has a characteristic of blocking a wavelength band of the first excitation light and a wavelength band of the second excitation light and a characteristic of transmitting a wavelength band of the visible light, a wavelength band of first fluorescence, and a wavelength band of second fluorescence. An imaging unit is configured to capture an image of the visible light, the first fluorescence, and the second fluorescence and configured to output a first imaging signal and a second imaging signal.

11 Claims, 20 Drawing Sheets

(51) Int. Cl.
  *A61B 1/06*  (2006.01)
  *A61B 1/05*  (2006.01)
(52) U.S. Cl.
  CPC .......... *A61B 1/0638* (2013.01); *A61B 1/0646* (2013.01); *A61B 1/0653* (2013.01); *A61B 1/0684* (2013.01)

(56) References Cited

U.S. PATENT DOCUMENTS

| | | | | |
|---|---|---|---|---|
| 2002/0175993 | A1* | 11/2002 | Ueno | A61B 1/00186 348/68 |
| 2002/0177751 | A1* | 11/2002 | Ueno | A61B 5/0071 600/476 |
| 2004/0186351 | A1* | 9/2004 | Imaizumi | A61B 1/0005 600/476 |
| 2005/0027166 | A1* | 2/2005 | Matsumoto | A61B 1/00186 977/852 |
| 2006/0247537 | A1* | 11/2006 | Matsumoto | A61B 1/00186 600/478 |
| 2007/0046778 | A1* | 3/2007 | Ishihara | G01N 21/6428 348/68 |
| 2008/0039695 | A1* | 2/2008 | Takaoka | A61B 5/0071 600/178 |
| 2008/0039697 | A1 | 2/2008 | Morishita | |
| 2008/0177140 | A1* | 7/2008 | Cline | A61B 1/05 600/112 |
| 2008/0267472 | A1* | 10/2008 | Demos | A61B 5/0086 382/128 |
| 2009/0236541 | A1* | 9/2009 | Lomnes | A61B 1/0646 250/362 |
| 2009/0268010 | A1* | 10/2009 | Zhao | A61B 1/00186 348/E13.001 |
| 2009/0289200 | A1* | 11/2009 | Ishii | A61B 1/00009 250/459.1 |
| 2010/0036203 | A1* | 2/2010 | Nakaoka | A61B 5/0084 600/178 |
| 2010/0084563 | A1* | 4/2010 | Ohno | A61B 5/0071 250/363.01 |
| 2010/0268091 | A1* | 10/2010 | Takaoka | A61B 1/0646 600/478 |
| 2011/0077465 | A1 | 3/2011 | Mizuyoshi et al. | |
| 2011/0235324 | A1* | 9/2011 | Irion | A61B 1/07 362/249.02 |
| 2012/0259174 | A1* | 10/2012 | Yamamoto | A61B 1/063 600/109 |
| 2013/0053703 | A1* | 2/2013 | Yamamoto | A61B 1/0638 600/476 |
| 2013/0075607 | A1* | 3/2013 | Bikumandla | H01L 27/14634 257/E31.127 |
| 2013/0289373 | A1* | 10/2013 | Yamamoto | A61B 5/14551 600/339 |
| 2013/0338438 | A1* | 12/2013 | Watanabe | A61B 1/0002 600/109 |
| 2014/0171764 | A1* | 6/2014 | Kim | A61B 90/361 600/317 |
| 2014/0240566 | A1* | 8/2014 | Shizukuishi | H01L 27/14605 438/66 |
| 2015/0148630 | A1* | 5/2015 | Meester | A61B 1/00009 600/317 |
| 2016/0256039 | A1* | 9/2016 | Fukunaga | H04N 9/07 |
| 2016/0262602 | A1* | 9/2016 | Yu | A61B 1/043 |
| 2017/0167980 | A1* | 6/2017 | Dimitriadis | A61B 3/14 |
| 2017/0172393 | A1* | 6/2017 | Fukunaga | H04N 5/2256 |
| 2017/0251912 | A1* | 9/2017 | Kato | A61B 1/00009 |
| 2018/0049633 | A1* | 2/2018 | Fukunaga | H04N 5/2256 |
| 2018/0199018 | A1* | 7/2018 | Fukunaga | H04N 9/07 |
| 2019/0110686 | A1* | 4/2019 | Kato | A61B 1/00096 |
| 2019/0216325 | A1* | 7/2019 | Ouyang | A61B 1/0684 |

FOREIGN PATENT DOCUMENTS

| | | |
|---|---|---|
| JP | 2008-43396 A | 2/2008 |
| JP | 2008-148791 A | 7/2008 |
| JP | 2011-147757 A | 8/2011 |
| JP | 2013-248319 A | 12/2013 |
| JP | 2015-99875 A | 5/2015 |
| WO | 2017/047140 A1 | 3/2017 |

\* cited by examiner

RELATED ART

ENDOSCOPE DEVICE

The present application is a continuation application based on International Patent Application No. PCT/JP2017/020796 filed on Jun. 5, 2017, the contents of which is incorporated herein by reference.

BACKGROUND OF THE INVENTION

Field of the Invention

The present invention relates to an endoscope device.

Description of Related Art

A fluorescent endoscope device that is able to acquire a visible light image and a fluorescent image in a system. The visible light image is used for acquiring form information of an object for observation that is a living body or the like. The fluorescent image is used for diagnosing whether or not a tumor is present inside a living body.

A fluorescent endoscope device disclosed in Japanese Unexamined Patent Application, First Publication No. 2006-296635 is able to acquire a plurality of types of fluorescent images in addition to a visible light. The fluorescent images are based on self-fluorescence originally present inside a living body, fluorescence due to a fluorescent agent administered inside a body, and the like. For example, in Japanese Unexamined Patent Application, First Publication No. 2006-296635, a fluorescent image that is based on self-fluorescence from collagen irradiated with certain excitation light is acquired and a fluorescent image that is based on fluorescence from a tumor irradiated with other excitation light is acquired. The self-fluorescence from collagen is fluorescence from Alexa 680 that is an administered fluorescent agent. In a case where a plurality of types of fluorescent images can be acquired in addition to a normal visible light as with the fluorescent endoscope device shown in Japanese Unexamined Patent Application, First Publication No. 2006-296635, it is possible to further improve performance for diagnosis whether or not a tumor is present and the like.

Details of the fluorescent endoscope device disclosed in Japanese Unexamined Patent Application, First Publication No. 2006-296635 will be described. An excitation wavelength selection filter 60 shown in FIG. 30 is disposed at the back of a light source. FIG. 30 shows a configuration of the excitation wavelength selection filter 60. The excitation wavelength selection filter 60 includes a first filter 61, a second filter 62, and a third filter 63. The excitation wavelength selection filter 60 rotates around a rotation axis 64.

FIG. 31 shows spectral transmission characteristics of the first filter 61. In FIG. 31, the horizontal axis of the graph represents a wavelength and the vertical axis of the graph represents transmittance. As shown in FIG. 31, the first filter 61 transmits only light of a wavelength band of which the wavelength is approximately 400 nm. In other words, the first filter 61 transmits only light that excites collagen. Hereinafter, light that excites collagen is defined as first excitation light.

FIG. 32 shows spectral transmission characteristics of the second filter 62. In FIG. 32, the horizontal axis of the graph represents a wavelength and the vertical axis of the graph represents transmittance. As shown in FIG. 32, the second filter 62 transmits only light of a wavelength band of which the wavelength is approximately 680 nm. In other words, the second filter 62 transmits only light that excites Alexa 680. Hereinafter, light that excites Alexa 680 is defined as second excitation light.

FIG. 33 shows spectral transmission characteristics of the third filter 63. In FIG. 33, the horizontal axis of the graph represents a wavelength and the vertical axis of the graph represents transmittance. As shown in FIG. 33, the third filter 63 transmits only light of a wavelength band of which the wavelength is approximately 400 nm to approximately 600 nm. In other words, the third filter 63 transmits only visible light.

An excitation wavelength blocking filter is disposed in front of an imaging device. FIG. 34 shows spectral transmission characteristics of the excitation wavelength blocking filter. The excitation wavelength blocking filter blocks first excitation light and second excitation light, and transmits visible light, fluorescence from collagen, and fluorescence from Alexa 680. Hereinafter, fluorescence from collagen is defined as first fluorescence and fluorescence from Alexa 680 is defined as second fluorescence.

FIG. 35 shows spectral characteristics of excitation light and fluorescence. In FIG. 35, the horizontal axis of the graph represents a wavelength and the vertical axis of the graph represents excitation light intensity or fluorescence intensity. First excitation light E1001 is light that excites collagen. Second excitation light E1002 is light that excites Alexa 680. First fluorescence F1001 is fluorescence that is emitted from collagen irradiated with the first excitation light E1001. Second fluorescence F1002 is fluorescence that is emitted from Alexa 680 irradiated with the second excitation light E1002.

When the excitation wavelength selection filter 60 rotates, visible light, first excitation light, and second excitation light are sequentially radiated on a living body. In this way, reflected light from the living body, first fluorescence excited by the first excitation light, and second fluorescence excited by the second excitation light are sequentially emitted. Reflected light of the first excitation light and reflected light of the second excitation light are blocked by the excitation wavelength blocking filter disposed in front of the imaging device. For this reason, the imaging device is able to sequentially acquire the reflected light (visible light) from the living body, the first fluorescence, and the second fluorescence.

SUMMARY OF THE INVENTION

According to a first aspect of the present invention, an endoscope device includes a light source unit, an imaging unit, an excitation wavelength blocking filter, and a signal processing unit. The light source unit is configured to sequentially emit first illumination light and second illumination light. The first illumination light includes visible light. The second illumination light includes first excitation light for exciting a first fluorescent substance existing inside an object for observation. At least the second illumination light out of the first illumination light and the second illumination light includes second excitation light for exciting a second fluorescent substance existing inside the object. The imaging unit is configured to capture an image of reflected light that is the visible light reflected by the object, first fluorescence excited by the first excitation light and emitted from the object, and second fluorescence excited by the second excitation light and emitted from the object and is configured to output a first imaging signal and a second imaging signal. The first imaging signal is generated on the basis of the reflected light. The second imaging signal is generated on the basis of the first fluorescence. At least the second imaging signal out of the first imaging signal and the second imaging signal is further generated on the basis of the second fluorescence. The excitation wavelength blocking filter is disposed on an optical path from the object to the imaging unit and has a characteristic of blocking a wavelength band of the first excitation light and a wavelength band of the second excitation light and a characteristic of transmitting a wavelength band of the visible light, a wavelength band of the first fluorescence, and a wavelength band of the second fluorescence. The signal processing unit is configured to generate a visible light image that is based on the reflected light, a first fluorescent image that is based on the first fluorescence, and a second fluorescent image that is based on the second fluorescence on the basis of the first imaging signal and the second imaging signal output from the imaging unit.

According to a second aspect of the present invention, in the first aspect, the light source unit may include a light source and a rotation filter. The light source may be configured to emit light of a wavelength band including at least the wavelength band of each of the visible light, the first excitation light, and the second excitation light. The rotation filter may be disposed on an optical path of light emitted from the light source and may include a first filter and a second filter disposed in a circumferential direction thereof. The first filter may be configured to transmit the visible light. The second filter may be configured to transmit the first excitation light. At least the second filter out of the first filter and the second filter may transmit the second excitation light.

According to a third aspect of the present invention, in the first aspect, the first illumination light may include the visible light and the second excitation light. The imaging unit may be configured to output a first signal and a second signal as the first imaging signal when the first illumination light is radiated on the object. The first signal may be generated on the basis of the reflected light. The second signal may be generated on the basis of the second fluorescence. The signal processing unit may be configured to generate the visible light image on the basis of the first signal and generate the second fluorescent image on the basis of the second signal when the first illumination light is radiated on the object. The second illumination light may include the first excitation light and the second excitation light. The imaging unit may be configured to output a third signal and a fourth signal as the second imaging signal when the second illumination light is radiated on the object. The third signal may be generated on the basis of the first fluorescence and the second fluorescence. The fourth signal may be generated on the basis of the second fluorescence. The signal processing unit may be configured to generate the first fluorescent image on the basis of the third signal and the fourth signal and generate the second fluorescent image on the basis of the fourth signal when the second illumination light is radiated on the object.

According to a fourth aspect of the present invention, in the third aspect, the imaging unit may include a first substrate, a second substrate stacked on the first substrate, and an optical filter. The first substrate may include a plurality of first pixels disposed two-dimensionally and may be configured to output the first signal and the third signal. The second substrate may include a plurality of second pixels disposed two-dimensionally and may be configured to output the second signal and the fourth signal. The imaging unit may be configured to output the first signal and the second signal when the first illumination light is radiated on the object. The imaging unit may be configured to output the third signal and the fourth signal when the second illumination light is radiated on the object. The optical filter may be disposed between the first substrate and the second substrate. The optical filter may have an optical characteristic of blocking a wavelength band of the visible light and a wavelength band of the first fluorescence and an optical characteristic of transmitting a wavelength band of the second fluorescence.

According to a fifth aspect of the present invention, in the first aspect, the first illumination light may include the visible light and the second excitation light. The imaging unit may be configured to output a first signal and a second signal as the first imaging signal when the first illumination light is radiated on the object. The first signal may be generated on the basis of the reflected light. The second signal may be generated on the basis of the second fluorescence. The signal processing unit may be configured to generate the visible light image on the basis of the first signal and generate the second fluorescent image on the basis of the second signal when the first illumination light is radiated on the object. The second illumination light may include the first excitation light and the second excitation light. The imaging unit may be configured to output a third signal and a fourth signal as the second imaging signal when the second illumination light is radiated on the object. The third signal may be generated on the basis of the first fluorescence. The fourth signal may be generated on the basis of the second fluorescence. The signal processing unit may be configured to generate the first fluorescent image on the basis of the third signal and generate the second fluorescent image on the basis of the fourth signal when the second illumination light is radiated on the object.

According to a sixth aspect of the present invention, in the fifth aspect, the endoscope device may further include a light separation device configured to separate the reflected light and the second fluorescence from each other and separate the first fluorescence and the second fluorescence from each other. The imaging unit may include a first imaging device and a second imaging device. The reflected light and the first fluorescence separated by the light separation device may be incident to the first imaging device. The second fluorescence separated by the light separation device may be incident to the second imaging device. The first imaging device may be configured to output the first signal and the second imaging device may be configured to output the second signal when the first illumination light is radiated on the object. The first imaging device may be configured to output the third signal and the second imaging device may be configured to output the fourth signal when the second illumination light is radiated on the object.

According to a seventh aspect of the present invention, in the first aspect, the light source unit may include a plurality of light emitting devices capable of selectively emitting light of a wavelength band including the wavelength band of at least one of the visible light, the first excitation light, and the second excitation light.

According to an eighth aspect of the present invention, in the seventh aspect, the light emitting device included in the plurality of light emitting devices may be a light emitting diode.

According to a ninth aspect of the present invention, an endoscope device includes a light source unit, an imaging unit, an excitation wavelength blocking filter, and a signal processing unit. The light source unit is configured to sequentially emit first illumination light and second illumination light. The first illumination light includes visible light and first excitation light for exciting a first fluorescent substance existing inside an object for observation. The second illumination light includes the visible light and second excitation light for exciting a second fluorescent substance existing inside the object. The imaging unit is configured to capture an image of reflected light that is the visible light reflected by the object, first fluorescence excited by the first excitation light and emitted from the object, and second fluorescence excited by the second excitation light and emitted from the object and configured to output a first imaging signal and a second imaging signal. The first imaging signal is generated on the basis of the reflected light and the first fluorescence. The second imaging signal is generated on the basis of the reflected light and the second fluorescence. The excitation wavelength blocking filter is disposed on an optical path from the object to the imaging unit and has a characteristic of blocking a wavelength band of the first excitation light and a wavelength band of the second excitation light and a characteristic of transmitting a wavelength band of the visible light, a wavelength band of the first fluorescence, and a wavelength band of the second fluorescence. The signal processing unit is configured to generate a visible light image that is based on the reflected light, a first fluorescent image that is based on the first fluorescence, and a second fluorescent image that is based on the second fluorescence on the basis of the first imaging signal and the second imaging signal output from the imaging unit.

According to a tenth aspect of the present invention, in the ninth aspect, the light source unit may include a light source and a rotation filter. The light source may be configured to emit light of a wavelength band including at least the wavelength band of each of the visible light, the first excitation light, and the second excitation light. The rotation filter may be disposed on an optical path of light emitted from the light source and may include a first filter and a second filter disposed in a circumferential direction thereof. The first filter may be configured to transmit the visible light and the first excitation light. The second filter may be configured to transmit the visible light and the second excitation light.

According to an eleventh aspect of the present invention, in the ninth aspect, the imaging unit may be configured to output a first signal and a second signal as the first imaging signal when the first illumination light is radiated on the object. The first signal may be generated on the basis of the reflected light. The second signal may be generated on the basis of the first fluorescence. The signal processing unit may be configured to generate the visible light image on the basis of the first signal and generate the first fluorescent image on the basis of the second signal when the first illumination light is radiated on the object. The imaging unit may be configured to output a third signal and a fourth signal as the second imaging signal when the second illumination light is radiated on the object. The third signal may be generated on the basis of the reflected light. The fourth signal may be generated on the basis of the second fluorescence. The signal processing unit may be configured to generate the first fluorescent image on the basis of the third signal and generate the second fluorescent image on the basis of the fourth signal when the second illumination light is radiated on the object.

According to a twelfth aspect of the present invention, in the eleventh aspect, the imaging unit may include a first substrate, a second substrate stacked on the first substrate, and an optical filter. The first substrate may include a plurality of first pixels disposed two-dimensionally and may be configured to output the first signal and the third signal. The second substrate may include a plurality of second pixels disposed two-dimensionally and may be configured to output the second signal and the fourth signal. The imaging unit may be configured to output the first signal and the second signal when the first illumination light is radiated on the object. The imaging unit may be configured to output the third signal and the fourth signal when the second illumination light is radiated on the object. The optical filter may be disposed between the first substrate and the second substrate. The optical filter may have an optical characteristic of blocking a wavelength band of the visible light and an optical characteristic of transmitting a wavelength band of the first fluorescence and a wavelength band of the second fluorescence.

According to a thirteenth aspect of the present invention, in the eleventh aspect, the endoscope device may further include a light separation device configured to separate the reflected light and the first fluorescence from each other and separate the reflected light and the second fluorescence from each other. The imaging unit may include a first imaging device and a second imaging device. The reflected light separated by the light separation device may be incident to the first imaging device. The first fluorescence and the second fluorescence separated by the light separation device may be incident to the second imaging device. The first imaging device may be configured to output the first signal and the second imaging device may be configured to output the second signal when the first illumination light is radiated on the object. The first imaging device may be configured to output the third signal and the second imaging device may be configured to output the fourth signal when the second illumination light is radiated on the object.

According to a fourteenth aspect of the present invention, in the ninth aspect, the light source unit may include a plurality of light emitting devices capable of selectively emitting light of a wavelength band including the wavelength band of at least one of the visible light, the first excitation light, and the second excitation light.

According to a fifteenth aspect of the present invention, in the fourteenth aspect, the light emitting device included in the plurality of light emitting devices may be a light emitting diode.

According to a sixteenth aspect of the present invention, in the first to fifteenth aspects, the first fluorescent substance may be collagen and the second fluorescent substance may be Alexa 680.

According to a seventeenth aspect of the present invention, in the first to fifteenth aspects, the first fluorescent substance may be protoporphyrin IX and the second fluorescent substance may be indocyanine green.

According to an eighteenth aspect of the present invention, in the first to seventeenth aspects, the signal processing unit may be configured to generate a display image including the visible light image and at least one of the first fluorescent image and the second fluorescent image such that the visible light image and at least one of the first fluorescent image and the second fluorescent image are separated from each other in the display image.

According to a nineteenth aspect of the present invention, in the first to seventeenth aspects, the signal processing unit may be configured to generate a display image including the visible light image and at least one of the first fluorescent image and the second fluorescent image such that at least part of the visible light image and at least part of at least one of the first fluorescent image and the second fluorescent image overlap each other in the display image.

DETAILED DESCRIPTION OF THE INVENTION

Hereinafter, embodiments of the present invention will be described with reference to the drawings.

First Embodiment

In a first embodiment, a case where self-fluorescence from collagen shown in the description of related art and fluorescence from Alexa 680 that is a fluorescent agent are detected will be described. Alexa 680 has affinity with a tumor and is administered to a living body in advance.

Figure 23:
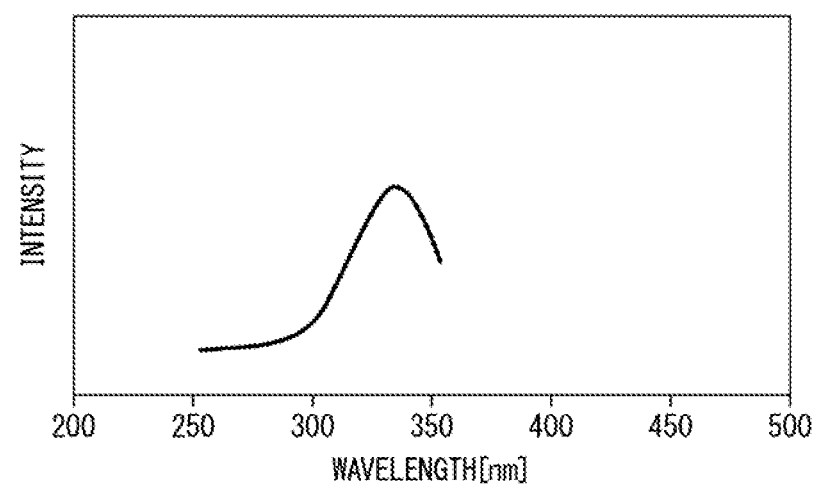
FIG. 23 is a graph showing excitation light absorption characteristics of collagen.
Figure 24:
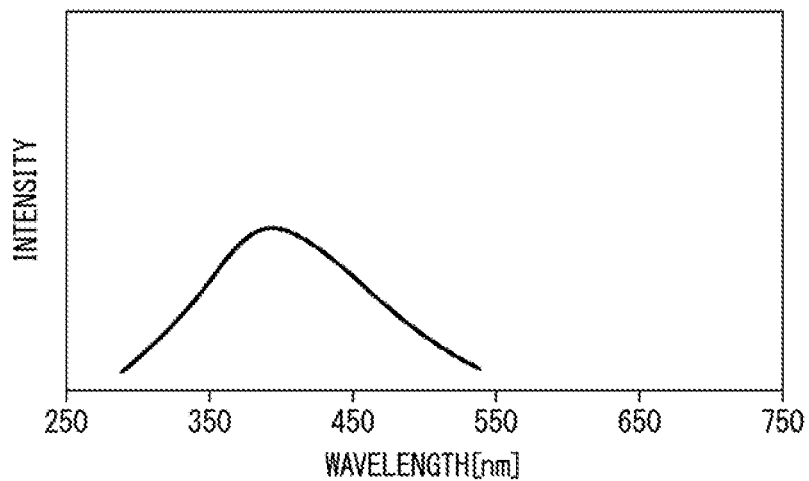
FIG. 24 is a graph showing fluorescence spectrum of collagen.

FIG. 23 shows excitation light absorption characteristics of collagen. FIG. 24 shows fluorescence spectrum of collagen. In FIG. 23 and FIG. 24, the horizontal axis of the graph represents a wavelength and the vertical axis of the graph represents intensity.

As shown in FIG. 23, the wavelength of excitation light at which the intensity of self-fluorescence of collagen is highest is approximately 340 nm. As shown in FIG. 24, the wavelength at which the intensity of self-fluorescence of collagen is highest is approximately 380 nm. Therefore, when excitation light having wavelengths of 300 nm to 350 nm is radiated toward the inside of a living body and light having wavelengths of 380 nm to 550 nm is detected, self-fluorescence of collagen can be detected.

Figure 25:
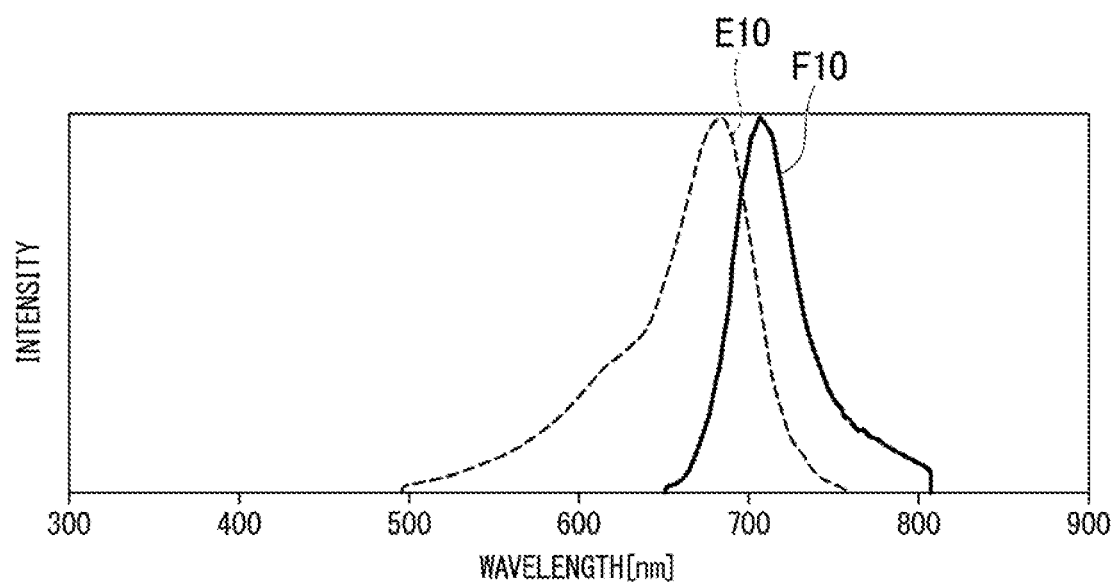
FIG. 25 is a graph showing excitation light absorption characteristics and fluorescence spectrum of Alexa 680.

FIG. 25 shows excitation light absorption characteristics and fluorescence spectrum of Alexa 680. In FIG. 25, the horizontal axis of the graph represents a wavelength and the vertical axis of the graph represents intensity. A line E10 represents excitation light absorption characteristics of Alexa 680. A line F10 represents fluorescence spectrum of Alexa 680.

As shown in FIG. 25, the wavelength of excitation light at which the intensity of fluorescence emitted from Alexa 680 is highest is approximately 680 nm and the wavelength at which the intensity of fluorescence emitted from Alexa 680 is highest is approximately 703 nm. Therefore, when excitation light having wavelengths of 650 nm to 690 nm is radiated toward the inside of a living body and light having wavelengths of 700 nm or more is detected, fluorescence emitted from Alexa 680 can be detected.

Figure 1:
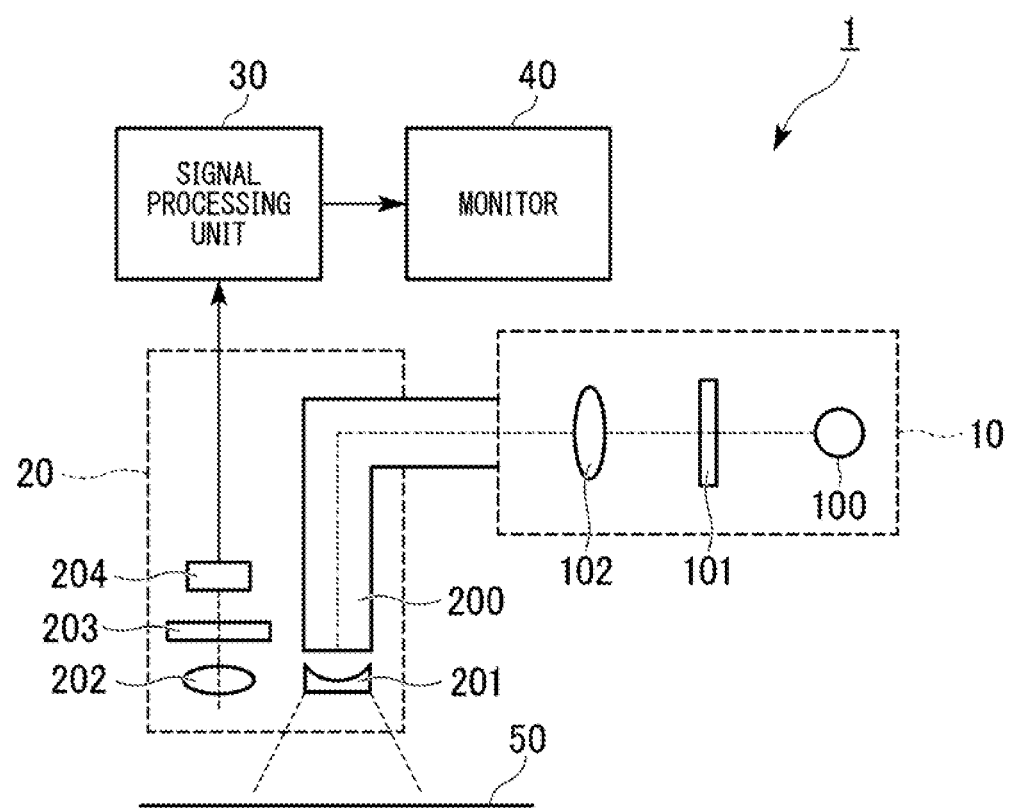
FIG. 1 is a block diagram showing a hardware configuration of an endoscope device according to a first embodiment of the present invention.

FIG. 1 shows a hardware configuration of an endoscope device 1 according to a first embodiment of the present invention. A schematic configuration of the endoscope device 1 will be described.

The endoscope device 1 includes a light source unit 10, an imaging device 204, an excitation wavelength blocking filter 203, and a signal processing unit 30. The light source unit 10 emits visible light, first excitation light for exciting a first fluorescent substance existing inside a subject 50, and second excitation light for exciting a second fluorescent substance existing inside the subject 50. The subject 50 is an object for observation inside a living body. The imaging device 204 captures an image of reflected light that is the visible light reflected by the subject 50, first fluorescence excited by the first excitation light and emitted from the subject 50, and second fluorescence excited by the second excitation light and emitted from the subject 50. The imaging device 204 outputs a first imaging signal and a second imaging signal. The excitation wavelength blocking filter 203 is disposed on an optical path from the subject 50 to the imaging device 204. The excitation wavelength blocking filter 203 has a characteristic of blocking a wavelength band of the first excitation light and a wavelength band of the second excitation light and a characteristic of transmitting a wavelength band of the visible light, a wavelength band of the first fluorescence, and a wavelength band of the second fluorescence. The signal processing unit 30 generates a visible light image that is based on the reflected light of the visible light, a first fluorescent image that is based on the first fluorescence, and a second fluorescent image that is based on the second fluorescence on the basis of the first imaging signal and the second imaging signal output from the imaging device 204.

The light source unit 10 sequentially emits first illumination light and second illumination light. The first illumination light includes the visible light. The second illumination light includes the first excitation light. At least one of the first illumination light and the second illumination light includes the second excitation light. The first imaging signal is based on the reflected light of the visible light. The second imaging signal is based on the first fluorescence. At least one of the first imaging signal and the second imaging signal is further based on the second fluorescence.

A detailed configuration of the endoscope device 1 will be described. As shown in FIG. 1, the endoscope device 1 includes the light source unit 10, a scope unit 20, the signal processing unit 30 (calculation device), and a monitor 40.

The light source unit 10 includes a light source 100, an excitation wavelength selection filter 101, and a condenser lens 102. The light source 100 emits light of a wavelength band including at least a wavelength band of each of the visible light, the first excitation light, and the second excitation light. The first excitation light is light for exciting the first fluorescent substance. In the first embodiment, the first fluorescent substance is collagen. The second excitation light is light for exciting the second fluorescent substance. In the first embodiment, the second fluorescent substance is Alexa 680. For example, the light source 100 emits white light.

The excitation wavelength selection filter 101 is disposed on the optical path of light emitted from the light source 100.

Figure 2:
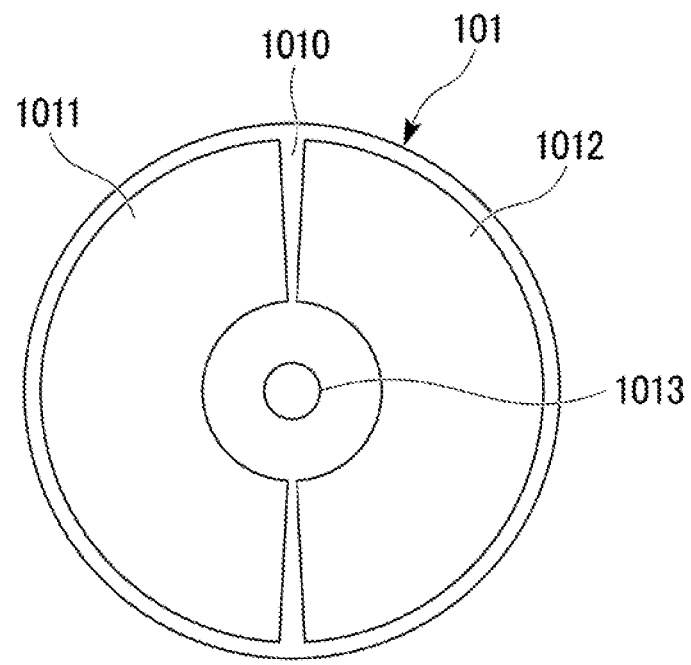
FIG. 2 is a schematic diagram showing a configuration of an excitation wavelength selection filter according to the first embodiment of the present invention.

FIG. 2 shows a configuration of the excitation wavelength selection filter 101. In FIG. 2, the configuration of the excitation wavelength selection filter 101 when the excitation wavelength selection filter 101 is seen in a direction approximately parallel to the optical path is schematically shown.

The excitation wavelength selection filter 101 includes a support plate 1010 in which a first filter 1011 and a second filter 1012 are disposed. For example, the first filter 1011 and the second filter 1012 are disposed on the surface of the support plate 1010. The first filter 1011 and the second filter 1012 are disposed around a rotation axis 1013. The first filter 1011 and the second filter 1012 are disposed in a circumferential direction of the rotation axis 1013. Due to drive of a motor not shown, the excitation wavelength selection filter 101 rotates around the rotation axis 1013. Therefore, the excitation wavelength selection filter 101 is constituted as a rotation filter. The first filter 1011 and the second filter 1012 are disposed in a rotation direction.

In the example shown in FIG. 2, the support plate 1010 is a disk. The shape of the support plate 1010 is not limited to a circle.

The first filter 1011 transmits the visible light. The second filter 1012 transmits the first excitation light. At least one of the first filter 1011 and the second filter 1012 transmits the second excitation light. In the example shown in the first embodiment, both the first filter 1011 and the second filter 1012 transmit the second excitation light. Therefore, the first filter 1011 transmits the visible light and the second excitation light and blocks light of a wavelength band other than the wavelength bands of those pieces of light. The second filter 1012 transmits the first excitation light and the second excitation light and blocks light of a wavelength band other than the wavelength bands of those pieces of light.

When the excitation wavelength selection filter 101 rotates, the first filter 1011 and the second filter 1012 are sequentially disposed on the optical path. Therefore, light transmitted through the first filter 1011 and light transmitted through the second filter 1012 are incident to the subject 50 in chronological order.

Figure 3:
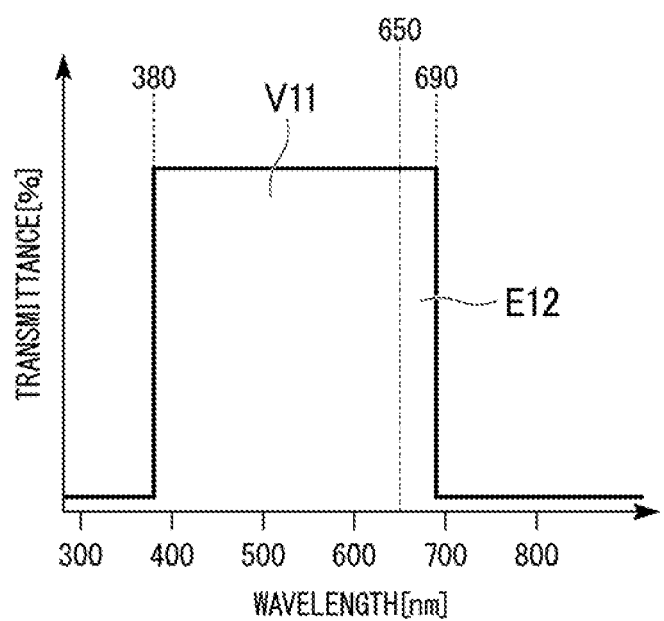
FIG. 3 is a graph showing spectral transmission characteristics of a first filter in the excitation wavelength selection filter according to the first embodiment of the present invention.

FIG. 3 shows spectral transmission characteristics of the first filter 1011. In FIG. 3, the horizontal axis of the graph represents a wavelength and the vertical axis of the graph represents transmittance. As shown in FIG. 3, a transmission wavelength band of the first filter 1011 includes a wavelength band V11 of 380 nm to 650 nm and a wavelength band E12 of 650 nm to 690 nm. The wavelength band V11 corresponds to the visible light. The wavelength band E12 corresponds to the second excitation light for exciting Alexa 680. The first filter 1011 blocks light of a wavelength band other than the wavelength band V11 and the wavelength band E12. Therefore, the first filter 1011 transmits only the visible light and the second excitation light.

Figure 4:
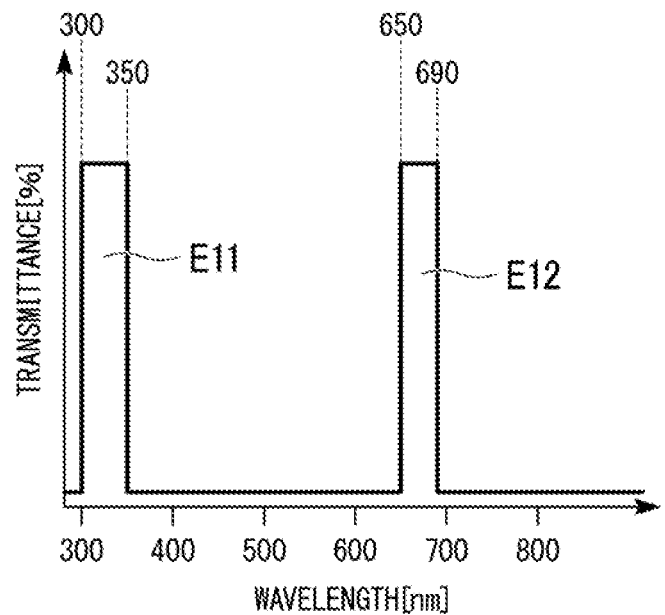
FIG. 4 is a graph showing spectral transmission characteristics of a second filter in the excitation wavelength selection filter according to the first embodiment of the present invention.

FIG. 4 shows spectral transmission characteristics of the second filter 1012. In FIG. 4, the horizontal axis of the graph represents a wavelength and the vertical axis of the graph represents transmittance. As shown in FIG. 4, a transmission wavelength band of the second filter 1012 includes a wavelength band E11 of 300 nm to 350 nm and a wavelength band E12 of 650 nm to 690 nm. The wavelength band E11 corresponds to the first excitation light for exciting collagen. The second filter 1012 blocks light of a wavelength band other than the wavelength band E11 and the wavelength band E12. In other words, the second filter 1012 transmits only the first excitation light and the second excitation light.

The condenser lens 102 causes light transmitted through the excitation wavelength selection filter 101 to be incident to the scope unit 20.

The scope unit 20 includes a light guide 200, an illumination lens 201, an objective lens 202, an excitation wavelength blocking filter 203, and an imaging device 204 (image sensor). Light from the light source 100 is incident to the light guide 200 through the excitation wavelength selection filter 101 and the condenser lens 102. The light guide 200 transmits the light from the light source 100 to the distal end of the scope unit 20. The light transmitted by the light guide 200 is radiated on the subject 50 by the illumination lens 201.

Light of a predetermined wavelength is radiated on the subject 50 due to the spectral transmission characteristics of the excitation wavelength selection filter 101. When the first filter 1011 is disposed on the optical path, the first illumination light is radiated on the subject 50. The first illumination light includes the visible light and the second excitation light. When the second filter 1012 is disposed on the optical path, the second illumination light is radiated on the subject 50. The second illumination light includes the first excitation light and the second excitation light. The light source unit 10 sequentially emits the first illumination light and the second illumination light.

At the distal end of the scope unit 20, the objective lens 202 is installed adjacent to the illumination lens 201. Light reflected by the subject 50 and fluorescence emitted from a fluorescent substance within the subject 50 are incident to the objective lens 202. The objective lens 202 captures an image of light from the subject 50. The objective lens 202 is disposed between the subject 50 and the imaging device 204 and the excitation wavelength blocking filter 203 is disposed between the objective lens 202 and the imaging device 204.

The excitation wavelength blocking filter 203 has a characteristic of blocking a wavelength band of the first excitation light and a wavelength band of the second excitation light and has a characteristic of transmitting a wavelength band of the visible light, a wavelength band of the first fluorescence, and a wavelength band of the second fluorescence. The visible light, the first excitation light, and the second excitation light are reflected by the subject 50 and incident to the excitation wavelength blocking filter 203. The first fluorescence is excited by the first excitation light, emitted from the subject 50, and incident to the excitation wavelength blocking filter 203. The second fluorescence is excited by the second excitation light, emitted from the subject 50, and incident to the excitation wavelength blocking filter 203.

Figure 5:
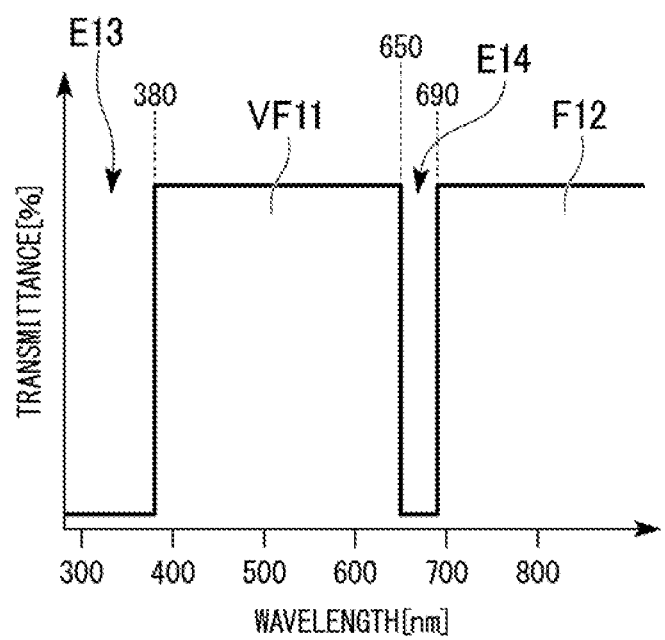
FIG. 5 is a graph showing spectral transmission characteristics of an excitation wavelength blocking filter according to the first embodiment of the present invention.

FIG. 5 shows spectral transmission characteristics of the excitation wavelength blocking filter 203. In FIG. 5, the horizontal axis of the graph represents a wavelength and the vertical axis of the graph represents transmittance. As shown in FIG. 5, a blocking wavelength band of the excitation wavelength blocking filter 203 includes a wavelength band E13 of 380 nm or less and a wavelength band E14 of 650 nm to 690 nm. The wavelength band E13 includes the wavelength band E11 of the first excitation light shown in FIG. 4. The wavelength band E14 includes the wavelength band E12 of the second excitation light shown in FIG. 4. Therefore, the excitation wavelength blocking filter 203 blocks reflected light of the first excitation light and reflected light of the second excitation light.

As shown in FIG. 5, a transmission wavelength band of the excitation wavelength blocking filter 203 includes a wavelength band VF11 of 380 nm to 650 nm and a wavelength band F12 of 690 nm or more. The wavelength band VF11 includes a wavelength band of 380 nm to 650 nm corresponding to the visible light and a wavelength band of 380 nm to 550 nm corresponding to the first fluorescence. The wavelength band F12 includes a wavelength band of 700 nm to 800 nm corresponding to the second fluorescence. Therefore, the excitation wavelength blocking filter 203 transmits reflected light of the visible light, the first fluorescence, and the second fluorescence.

The imaging device 204 is disposed at the image forming position of the objective lens 202. Light passing through the objective lens 202 and the excitation wavelength blocking filter 203 is incident to the imaging device 204. Due to the spectral transmission characteristics of the excitation wavelength blocking filter 203, the reflected light of the visible light, the first fluorescence, and the second fluorescence are incident to the imaging device 204. The imaging device 204 constitutes an imaging section. The imaging device 204 generates an imaging signal by capturing an image of light incident to the imaging device 204. In other words, the imaging device 204 captures an image of the reflected light of the visible light, the first fluorescence, and the second fluorescence and generates the first imaging signal and the second imaging signal. The first imaging signal and the second imaging signal generated by the imaging device 204 are output to the signal processing unit 30.

The signal processing unit 30 is constituted by at least one of a processor and a logic circuit. For example, the processor is at least one of a central processing unit (CPU), a digital signal processor (DSP), and a graphics processing unit (GPU). For example, the logic circuit is at least one of an application specific integrated circuit (ASIC) and a field-programmable gate array (FPGA). The signal processing unit 30 may include one or a plurality of processors. The signal processing unit 30 may include one or a plurality of logic circuits. The signal processing unit 30 generates the visible light image that is based on the reflected light of the visible light, the first fluorescent image that is based on the first fluorescence, and the second fluorescent image that is based on the second fluorescence on the basis of the first imaging signal and the second imaging signal output from the imaging device 204.

The monitor 40 is any one of a liquid crystal display, an organic electro luminescence (EL) display, and the like. The monitor 40 displays the visible light image, the first fluorescent image, and the second fluorescent image.

The signal processing unit 30 generates a display image including the visible light image and at least one of the first fluorescent image and the second fluorescent image such that the visible light image and at least one of the first fluorescent image and the second fluorescent image are separated from each other in the display image. The monitor 40 displays the display image such that the visible light image and at least one of the first fluorescent image and the second fluorescent image are separated from each other.

For example, the signal processing unit 30 generates the display image including the visible light image and the first fluorescent image such that the visible light image and the first fluorescent image are separated from each other in the display image. The monitor 40 displays the display image such that the visible light image and the first fluorescent image are separated from each other. Alternatively, the signal processing unit 30 generates the display image including the visible light image and the second fluorescent image such that the visible light image and the second fluorescent image are separated from each other in the display image. The monitor 40 displays the display image such that the visible light image and the second fluorescent image are separated from each other. Alternatively, the signal processing unit 30 generates the display image including the visible light image, the first fluorescent image, and the second fluorescent image such that the visible light image, the first fluorescent image, and the second fluorescent image are separated from each other in the display image. The monitor 40 displays the display image such that the visible light image, the first fluorescent image, and the second fluorescent image are separated from each other.

The signal processing unit 30 may generate a display image including the visible light image and at least one of the first fluorescent image and the second fluorescent image such that at least part of the visible light image and at least part of at least one of the first fluorescent image and the second fluorescent image overlap each other in the display image. The monitor 40 may display the display image such that at least part of the visible light image and at least part of at least one of the first fluorescent image and the second fluorescent image overlap each other.

For example, the signal processing unit 30 generates the display image including the visible light image and the first fluorescent image such that at least part of the visible light image and at least part of the first fluorescent image overlap each other in the display image. The monitor 40 displays the display image such that at least part of the visible light image and at least part of the first fluorescent image overlap each other in the display image. Alternatively, the signal processing unit 30 generates the display image including the visible light image and the second fluorescent image such that at least part of the visible light image and at least part of the second fluorescent image overlap each other in the display image. The monitor 40 displays the display image such that at least part of the visible light image and at least part of the second fluorescent image overlap each other in the display image. Alternatively, the signal processing unit 30 generates the display image including the visible light image, the first fluorescent image, and the second fluorescent image such that at least part of the visible light image, at least part of the first fluorescent image, and at least part of the second fluorescent image overlap each other in the display image. The monitor 40 displays the display image such that at least part of the visible light image, at least part of the first fluorescent image, and at least part of the second fluorescent image overlap each other in the display image.

The first illumination light includes the visible light and the second excitation light. When the first illumination light is radiated on the subject 50, the imaging device 204 outputs a first signal and a second signal as the first imaging signal. The first signal is an imaging signal that is based on the reflected light of the visible light. The second signal is an imaging signal that is based on the second fluorescence. In other words, the first imaging signal includes the first signal and the second signal. When the first illumination light is radiated on the subject 50, the signal processing unit 30 generates the visible light image on the basis of the first signal and generates the second fluorescent image on the basis of the second signal.

The second illumination light includes the first excitation light and the second excitation light. When the second illumination light is radiated on the subject 50, the imaging device 204 outputs a third signal and a fourth signal as the second imaging signal. The third signal is an imaging signal that is based on the first fluorescence and the second fluorescence. The fourth signal is an imaging signal that is based on the second fluorescence. In other words, the second imaging signal includes the third signal and the fourth signal. When the second illumination light is radiated on the subject 50, the signal processing unit 30 generates the first fluorescent image on the basis of the third signal and the fourth signal and generates the second fluorescent image on the basis of the fourth signal.

Figure 6:
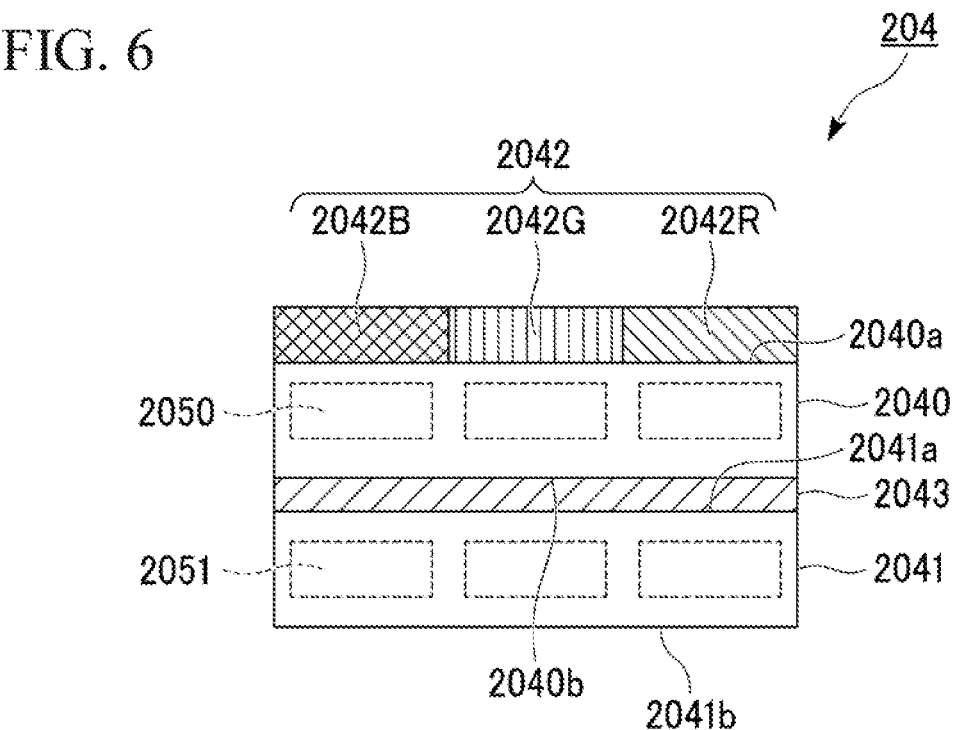
FIG. 6 is a cross-sectional view of an imaging device according to the first embodiment of the present invention.
Figure 7:
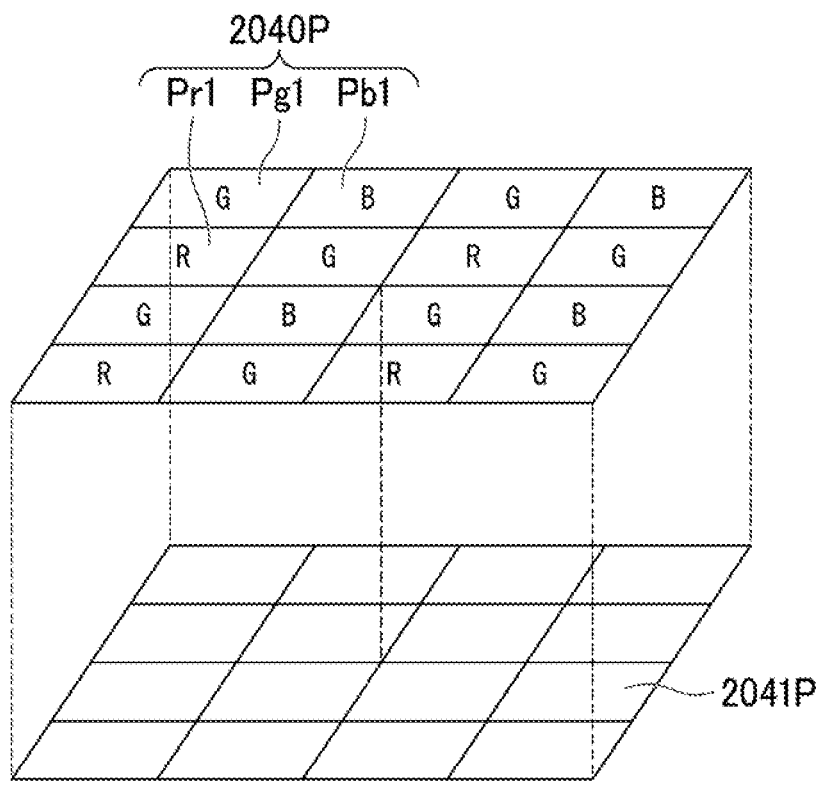
FIG. 7 is a reference diagram showing a pixel arrangement of the imaging device according to the first embodiment of the present invention.

FIG. 6 shows a configuration of the imaging device 204. In FIG. 6, the cross section of the imaging device 204 is shown. FIG. 7 shows a pixel arrangement of the imaging device 204. A schematic configuration of the imaging device 204 will be described.

The imaging device 204 includes a first substrate 2040, a second substrate 2041 stacked on the first substrate 2040, and an optical filter 2043. The first substrate 2040 includes a plurality of first pixels 2040P disposed two-dimensionally. The plurality of first pixels 2040P of the first substrate 2040 output the first signal and the third signal. The second substrate 2041 includes a plurality of second pixels 2041P disposed two-dimensionally. The plurality of second pixels 2041P of the second substrate 2041 output the second signal and the fourth signal.

When the first illumination light is radiated on the subject 50, the imaging device 204 outputs the first signal and the second signal. When the second illumination light is radiated on the subject 50, the imaging device 204 outputs the third signal and the fourth signal. The optical filter 2043 is disposed between the first substrate 2040 and the second substrate 2041. The optical filter 2043 has an optical characteristic of blocking a wavelength band of the visible light and a wavelength band of the first fluorescence and has an optical characteristic of transmitting a wavelength band of the second fluorescence.

The configuration of the imaging device 204 will be described in more detail. As shown in FIG. 6, the imaging device 204 includes the first substrate 2040, the second substrate 2041, a color filter 2042, and the optical filter 2043. These are stacked in the thickness direction of the first substrate 2040.

The first substrate 2040 and the second substrate 2041 are semiconductor substrates. For example, the first substrate 2040 and the second substrate 2041 contain silicon (Si). The first substrate 2040 includes a surface 2040*a* and a surface 2040*b*. The surface 2040*a* and the surface 2040*b* are main surfaces of the first substrate 2040. A main surface is a relatively larger surface out of a plurality of surfaces constituting the surface of a substrate. The surface 2040*a* and the surface 2040*b* face in opposite directions.

The second substrate 2041 includes a surface 2041*a* and a surface 2041*b*. The surface 2041*a* and the surface 2041*b* are main surfaces of the second substrate 2041. The surface 2041*a* and the surface 2041*b* face in opposite directions. The surface 2040*b* of the first substrate 2040 and the surface 2041*a* of the second substrate 2041 face each other. As shown in FIG. 1, the signal processing unit 30 is disposed outside the imaging device 204. At least one of the first substrate 2040 and the second substrate 2041 may include at least part of the signal processing unit 30.

The color filter 2042 is stacked on the surface 2040*a* of the first substrate 2040. The color filter 2042 includes a red filter 2042R, a green filter 2042G, and a blue filter 2042B. The imaging device 204 may not include the color filter 2042. The color filter 2042 has only to be disposed at any position on the optical path from the subject 50 to the first substrate 2040.

As shown in FIG. 7, the first substrate 2040 includes the plurality of first pixels 2040P disposed two-dimensionally. The second substrate 2041 includes the plurality of second pixels 2041P disposed two-dimensionally. As shown in FIG. 6, the first substrate 2040 includes a plurality of first photoelectric conversion elements 2050. The second substrate 2041 includes a plurality of second photoelectric conversion elements 2051. The first photoelectric conversion element 2050 and the second photoelectric conversion element 2051 are photodiodes. Each of the plurality of first pixels 2040P includes the first photoelectric conversion element 2050. Each of the plurality of second pixels 2041P includes the second photoelectric conversion element 2051.

The plurality of first pixels 2040P include an R pixel Pr1, a G pixel Pg1, and a B pixel Pb1. In FIG. 7, the first pixel 2040P specified as "R" is the R pixel Pr1. In FIG. 7, the first pixel 2040P specified as "G" is the G pixel Pg1. In FIG. 7, the first pixel 2040P specified as "B" is the B pixel Pb1.

The red filter 2042R is disposed on the surface of the R pixel Pr1. The R pixel Pr1 generates an R signal. The green filter 2042G is disposed on the surface of the G pixel Pg1. The G pixel Pg1 generates a G signal. The blue filter 2042B is disposed on the surface of the B pixel Pb1. The B pixel Pb1 generates a B signal. The pixel arrangement of the plurality of first pixels 2040P shown in FIG. 7 is the Bayer arrangement. In the Bayer arrangement, a basic arrangement is regularly and periodically disposed in the row direction and the column direction. The basic arrangement includes one R pixel Pr1, two G pixels Pg1, and one B pixel Pb1.

The first photoelectric conversion element 2050 converts light incident to the first pixel 2040P to a signal. The second photoelectric conversion element 2051 converts light incident to the second pixel 2041P to a signal.

The signal output from the first photoelectric conversion element 2050 corresponds to the first signal and the third signal. The signal output from the second photoelectric conversion element 2051 corresponds to the second signal and the fourth signal. Signals output from the plurality of first photoelectric conversion elements 2050 and signals output from the plurality of second photoelectric conversion elements 2051 are output to the signal processing unit 30.

Figure 26:
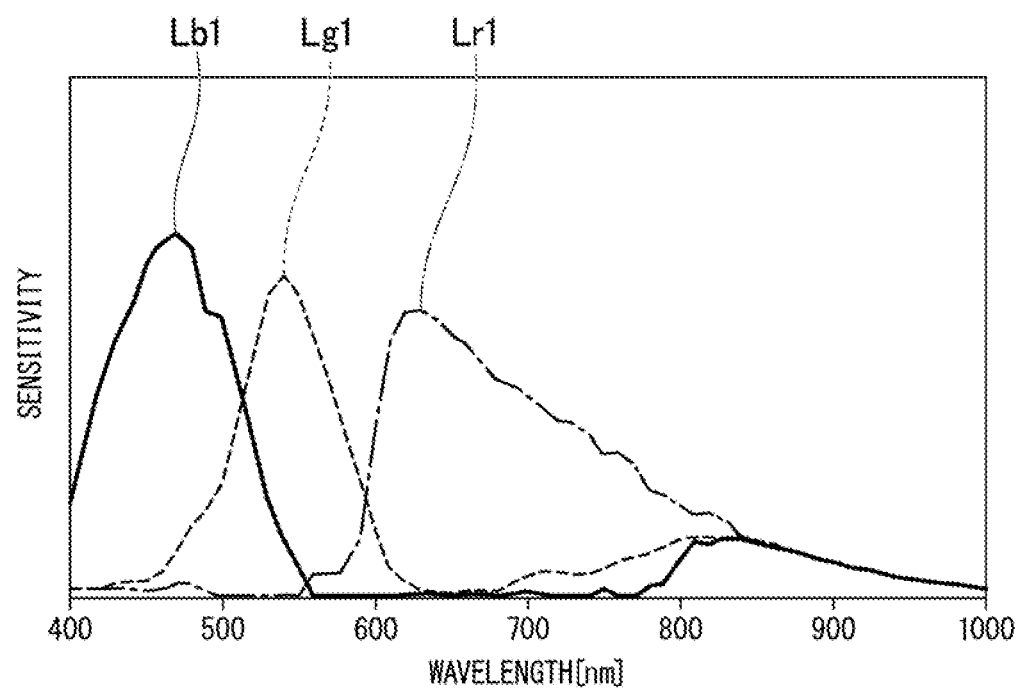
FIG. 26 is a graph showing spectral sensitivity characteristics of a pixel.

FIG. 26 shows spectral sensitivity characteristics of the R pixel Pr1, the G pixel Pg1, and the B pixel Ph1. In FIG. 26, the horizontal axis of the graph represents a wavelength and the vertical axis of the graph represents sensitivity.

A line Lb1 represents spectral sensitivity characteristics of the B pixel Pb1. As shown by the line Lb1, the B pixel Pb1 has sensitivity in part of a wavelength band of 380 nm to 650 nm corresponding to the visible light, a wavelength band of 380 nm to 550 nm corresponding to the first fluorescence, and part of a wavelength band of 700 nm to 800 nm corresponding to the second fluorescence. In other words, the B pixel Pb1 detects the reflected light of the visible light, the first fluorescence, and the second fluorescence.

A line Lg1 represents spectral sensitivity characteristics of the G pixel Pg1. As shown by the line Lg1, the G pixel Pg1 has sensitivity in part of a wavelength band of 380 nm to 650 nm corresponding to the visible light, a wavelength band of 380 nm to 550 nm corresponding to the first fluorescence, and a wavelength band of 700 nm to 800 nm corresponding to the second fluorescence. In other words, the G pixel Pg1 detects the reflected light of the visible light, the first fluorescence, and the second fluorescence.

A line Lr1 represents spectral transmission characteristics of the R pixel Pr1. As shown by the line Lr1, the R pixel Pr1 has sensitivity in part of a wavelength band of 380 nm to 650 nm corresponding to the visible light, a wavelength band of 380 nm to 550 nm corresponding to the first fluorescence, and a wavelength band of 700 nm to 800 nm corresponding to the second fluorescence. In other words, the R pixel Pr1 detects the reflected light of the visible light, the first fluorescence, and the second fluorescence.

Figure 8:
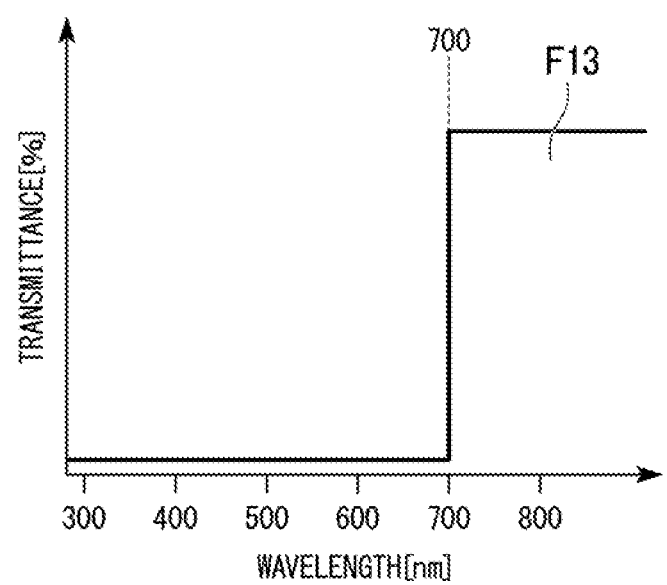
FIG. 8 is a graph showing spectral transmission characteristics of an optical filter according to the first embodiment of the present invention.

FIG. 8 shows spectral transmission characteristics of the optical filter 2043. In FIG. 8, the horizontal axis of the graph represents a wavelength and the vertical axis of the graph represents transmittance. As shown in FIG. 8, a transmission wavelength band of the optical filter 2043 includes a wavelength band F13 of 700 nm or more. The wavelength band F13 includes a wavelength band of 700 nm to 800 nm corresponding to the second fluorescence. The optical filter 2043 blocks light of a wavelength band other than the wavelength band F13. Therefore, the optical filter 2043 blocks the reflected light of the visible light and the first fluorescence and transmits the second fluorescence.

Light transmitted through the color filter 2042 is incident to the surface 2040a of the first substrate 2040. The first substrate 2040 is a backside-illumination type imaging substrate. For example, the thickness of the first substrate 2040 is several μm. In other words, the first substrate 2040 is thin. Light absorptivity of silicon differs according to a wavelength of light. Light absorptivity of silicon for light having a short wavelength is high. Light absorptivity of silicon for light having a long wavelength is low. Therefore, when the thickness of the first substrate 2040 is 3 part of light having wavelengths of 500 nm or more is not absorbed in the first substrate 2040 and is transmitted through the first substrate 2040.

Light having wavelengths of 500 nm or more and transmitted through the first substrate 2040 is incident to the optical filter 2043. Out of light incident to the optical filter 2043, light having wavelengths of 700 nm or more is transmitted through the optical filter 2043. In other words, the second fluorescence is transmitted through the optical filter 2043. The second fluorescence transmitted through the optical filter 2043 is incident to the surface 2041a of the second substrate 2041.

An operation of the endoscope device 1 will be described. When the excitation wavelength selection filter 101 rotates, the first illumination light transmitted through the first filter 1011 and the second illumination light transmitted through the second filter 1012 are sequentially radiated on the subject 50. The first illumination light includes the visible light and the second excitation light. The second illumination light includes the first excitation light and the second excitation light.

An operation of the endoscope device 1 when the first illumination light is radiated on the subject 50 will be described. Due to the spectral transmission characteristics of the first filter 1011 shown in FIG. 3, the visible light having wavelengths of 380 nm to 650 nm and the second excitation light having wavelengths of 650 nm to 690 nm are radiated on the subject 50. Reflected light of the visible light, reflected light of the second excitation light, and the second fluorescence having wavelengths of 700 nm to 800 nm are emitted from the subject 50.

The light emitted from the subject 50 is incident to the excitation wavelength blocking filter 203. The excitation wavelength blocking filter 203 blocks the reflected light of the second excitation light and transmits the reflected light of the visible light and the second fluorescence due to the spectral transmission characteristics shown in FIG. 5. The reflected light of the visible light and the second fluorescence transmitted through the excitation wavelength blocking filter 203 are incident to the imaging device 204.

The reflected light of the visible light and the second fluorescence are incident to the first photoelectric conversion element 2050 of each of the B pixel Pb1, the G pixel Pg1, and the R pixel Pr1 of the first substrate 2040. The second fluorescence is feeble enough to be ignored, compared to the reflected light of the visible light. For this reason, the plurality of first pixels 2040P of the first substrate 2040 output the first signal that is based on the reflected light of the visible light. The signal processing unit 30 generates the visible light image on the basis of the first signal.

Out of light incident to the imaging device 204, most of light having wavelengths of 500 nm or less is absorbed in the first substrate 2040 and only part of light having wavelengths of 500 nm or more is transmitted through the first substrate 2040. In other words, part of the reflected light of the visible light incident to the imaging device 204 and part of the second fluorescence incident to the imaging device 204 are transmitted through the first substrate 2040.

The light transmitted through the first substrate 2040 is incident to the optical filter 2043. The optical filter 2043 blocks the reflected light of the visible light transmitted through the first substrate 2040 and transmits the second fluorescence due to the spectral transmission characteristics shown in FIG. 8. The light transmitted through the optical filter 2043 is incident to the plurality of second photoelectric conversion elements 2051 of the second substrate 2041. The plurality of second pixels 2041P of the second substrate 2041 output the second signal that is based on the second fluorescence. The signal processing unit 30 generates the second fluorescent image on the basis of the second signal.

An operation of the endoscope device 1 when the second illumination light is radiated on the subject 50 will be described. Due to the spectral transmission characteristics of the second filter 1012 shown in FIG. 4, the first excitation light having wavelengths of 300 nm to 350 nm and the second excitation light having wavelengths of 650 nm to 690 nm are radiated on the subject 50. Reflected light of the first excitation light, reflected light of the second excitation light, the first fluorescence having wavelengths of 380 nm to 550 nm, and the second fluorescence having wavelengths of 700 nm to 800 nm are emitted from the subject 50.

The light emitted from the subject 50 is incident to the excitation wavelength blocking filter 203. The excitation wavelength blocking filter 203 blocks the reflected light of the first excitation light and the reflected light of the second excitation light and transmits the first fluorescence and the second fluorescence due to the spectral transmission characteristics shown in FIG. 5. The first fluorescence and the second fluorescence transmitted through the excitation wavelength blocking filter 203 are incident to the imaging device 204.

The first fluorescence and the second fluorescence are incident to the first photoelectric conversion element 2050 of each of the B pixel Pb1, the G pixel Pg1, and the R pixel Pr1 of the first substrate 2040. The plurality of first pixels 2040P of the first substrate 2040 output the third signal that is based on the first fluorescence and the second fluorescence.

Part of the first fluorescence incident to the imaging device 204 and part of the second fluorescence incident to the imaging device 204 are transmitted through the first substrate 2040. The light transmitted through the first substrate 2040 is incident to the optical filter 2043. The optical filter 2043 blocks the first fluorescence transmitted through the first substrate 2040 and transmits the second fluorescence due to the spectral transmission characteristics shown in FIG. 8. The light transmitted through the optical filter 2043 is incident to the plurality of second photoelectric conversion elements 2051 of the second substrate 2041. The plurality of second pixels 2041P of the second substrate 2041 output the fourth signal that is based on the second fluorescence. The signal processing unit 30 generates the second fluorescent image on the basis of the fourth signal. In addition, the signal processing unit 30 generates the first fluorescent image on the basis of the third signal and the fourth signal.

Here, in order for the first fluorescence and the second fluorescence to be incident to the first photoelectric conversion element 2050 of each pixel, it is necessary to separate the signal due to the first fluorescence and the signal due to the second fluorescence detected in the first photoelectric conversion element 2050 of each pixel from each other and to detect only the signal due to the first fluorescence. An example in which only the signal due to the first fluorescence is calculated will be described.

In the description below, $\alpha$ represents a rate at which the B pixel Pb1 of the first substrate 2040 absorbs the first fluorescence, $\beta$ represents a rate at which the B pixel Pb1 of the first substrate 2040 absorbs the second fluorescence, and $\gamma$ represents a rate at which the second pixel 2041P of the second substrate 2041 absorbs the second fluorescence. $\alpha$, $\beta$, and $\gamma$ can be calculated on the basis of the spectral sensitivity of the first substrate 2040 and the second substrate 2041. The ratio between $\beta$ and $\gamma$ is determined on the basis of the ratio between the spectral sensitivity of the B pixel Pb1 of the first substrate 2040 in the wavelength band of 700 nm to 800 nm corresponding to the second fluorescence and the spectral sensitivity of the second pixel 2041P of the second substrate 2041 in that wavelength band. $\alpha$, $\beta$, and $\gamma$ are parameters that are based on production conditions of the imaging device 204. For example, the production conditions include the thickness of each of the first substrate 2040 and the second substrate 2041 in the optical axis direction. Alternatively, the production conditions include the spectral transmission characteristics of the color filter 2042 and the optical filter 2043. $\alpha$, $\beta$, and $\gamma$ are real numbers 0 or more and 1 or less.

The B pixel Pb1 generates the third signal that is based on the first fluorescence and the second fluorescence. In the description below, the signal value of the third signal generated by the B pixel Ph1 is ($\alpha$B+$\beta$IR). $\alpha$B is the signal value that is based on the first fluorescence. $\beta$IR is the signal value that is based on the second fluorescence.

The second pixel 2041P generates the fourth signal that is based on the second fluorescence. In the description below, the signal value of the fourth signal generated by the second pixel 2041P is $\gamma$IR. $\gamma$IR is the signal value that is based on the second fluorescence. The fourth signal generated by the second pixel 2041P disposed at the position corresponding to the B pixel Pb1 is used. In other words, the fourth signal generated by the second pixel 2041P to which light transmitted through the B pixel Pb1 is incident is used.

The signal processing unit 30 multiplies the signal value of the fourth signal generated by the second pixel 2041P, that is, $\gamma$IR by the ratio of $\beta$ to $\gamma$, that is, ($\beta/\gamma$). In this way, the signal processing unit 30 can calculate the signal value $\beta$IR that is based on the second fluorescence detected by the first pixel 2040P. The signal processing unit 30 subtracts the signal value $\beta$IR calculated by using the above-described method from the signal value of the third signal ($\alpha$B+$\beta$IR) generated by the B pixel Pb1. In this way, the signal processing unit 30 generates the signal that is based on only the first fluorescence. The signal value of this signal is αB.

The signal processing unit 30 may add the second signal that is based on the second fluorescence and the fourth signal that is based on the second fluorescence together. In this way, the signal to noise (SN) ratio of the signal that is based on the second fluorescence is improved and the image quality of the second fluorescent image is improved.

Figure 9:
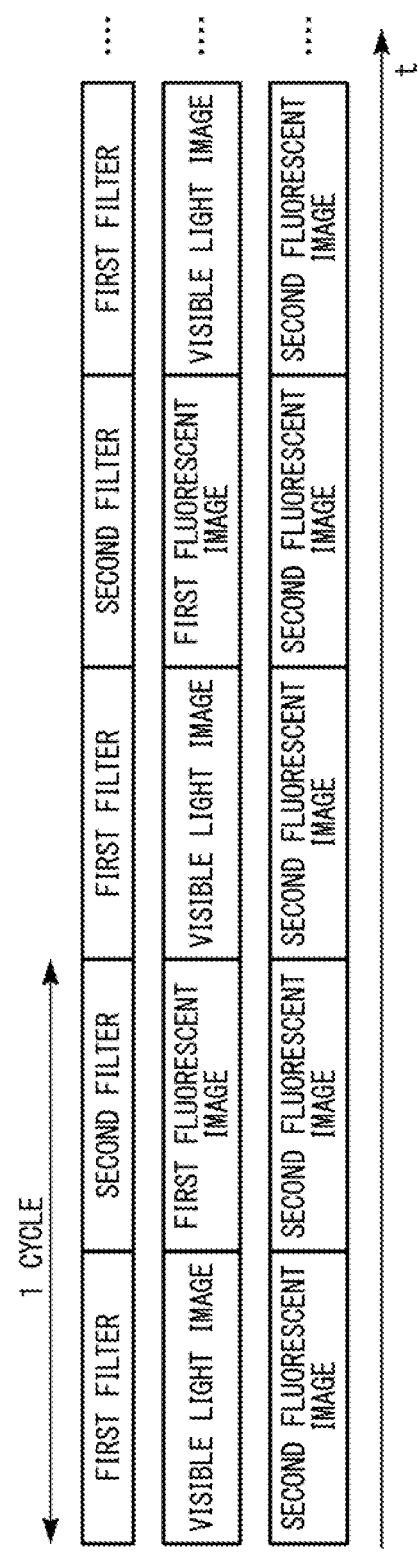
FIG. 9 is a timing chart showing an operation of the endoscope device according to the first embodiment of the present invention.

FIG. 9 is a timing chart showing the operation of the endoscope device 1. In FIG. 9, filter types of the excitation wavelength selection filter 101 disposed on the optical path are shown. In addition, in FIG. 9, an image that is based on the signal acquired in the first substrate 2040 and an image that is based on the signal acquired in the second substrate 2041 are shown. In FIG. 9, time passes in the right direction.

An operation in one cycle is repeated. In the first half period of the cycle, the first filter 1011 is disposed on the optical path. The first filter 1011 transmits the visible light and the second excitation light out of light emitted from the light source 100. The first illumination light including the visible light and the second excitation light is radiated on the subject 50. Reflected light of the visible light, reflected light of the second excitation light, and the second fluorescence are emitted from the subject 50 and incident to the imaging device 204. The reflected light of the visible light is detected in the first substrate 2040 and the second fluorescence is detected in the second substrate 2041. Consequently, the visible light image and the second fluorescent image are generated.

In the second half period of the cycle, the second filter 1012 is disposed on the optical path. The second filter 1012 transmits the first excitation light and the second excitation light out of light emitted from the light source 100. Reflected light of the first excitation light, reflected light of the second excitation light, the first fluorescence, and the second fluorescence are emitted from the subject 50 and incident to the imaging device 204. The first fluorescence is detected in the first substrate 2040 and the second fluorescence is detected in the second substrate 2041. Consequently, the first fluorescent image and the second fluorescent image are generated.

In the operation shown in FIG. 9, the second fluorescence is detected in the first half period and the second half period of one cycle. The second fluorescence may be detected in only the first half period or the second half period of one cycle.

The light source unit 10 may include a plurality of light emitting devices capable of selectively emitting light of a wavelength band including the wavelength band of at least one of the visible light, the first excitation light, and the second excitation light. For example, in a first period, at least one of the plurality of light emitting devices emits the visible light and the second excitation light. In a second period, at least one of the plurality of light emitting devices emits the first excitation light and the second excitation light. The light source unit 10 may include a first light emitting device that emits the visible light, a second light emitting device that emits the first excitation light, and a third light emitting device that emits the second excitation light. Each of the plurality of light emitting devices may be a light emitting diode.

The endoscope device 1 according to the first embodiment simultaneously captures an image of the reflected light of the visible light and the second fluorescence. Alternatively, the endoscope device 1 simultaneously captures an image of the first fluorescence and the second fluorescence. In this way, the interval of acquiring the visible light image is shortened. Therefore, the endoscope device 1 can suppress reduction of the frame rate of the visible light image and can acquire the visible light image and the plural types of fluorescent images.

The frame rate of the visible light image becomes faster compare to that of the related art. For this reason, the endoscope device 1 can suppress skipping of frames of the visible light image as much as possible. Consequently, moving images of the visible light image are easily watched and a user can easily understand the shape of an object for observation.

Modification Example of First Embodiment

Figure 10:
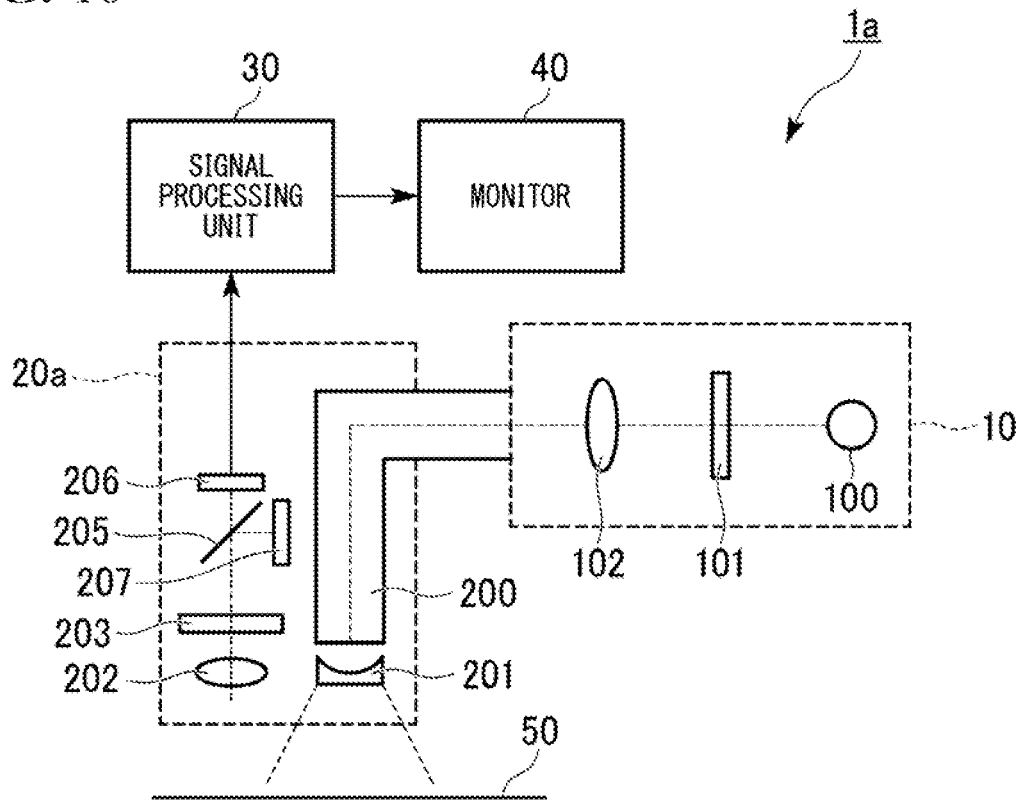
FIG. 10 is a block diagram showing a hardware configuration of an endoscope device according to a modified example of the first embodiment of the present invention.

FIG. 10 shows a hardware configuration of an endoscope device 1a according to a modification example of the first embodiment of the present invention.

A schematic configuration of the endoscope device 1a will be described. The endoscope device 1a includes a light source unit 10, an imaging device 206 (first imaging device), an imaging device 207 (second imaging device), an excitation wavelength blocking filter 203, and a signal processing unit 30. The light source unit 10 emits visible light, first excitation light, and second excitation light. The imaging device 206 captures an image of reflected light that is the visible light reflected by a subject 50 and first fluorescence excited by the first excitation light and emitted from the subject 50. The imaging device 207 captures an image of second fluorescence excited by the second excitation light and emitted from the subject 50. The imaging device 206 and the imaging device 207 output a first imaging signal and a second imaging signal. The excitation wavelength blocking filter 203 has a characteristic of blocking a wavelength band of the first excitation light and a wavelength band of the second excitation light and a characteristic of transmitting a wavelength band of the visible light, a wavelength band of the first fluorescence, and a wavelength band of the second fluorescence. The signal processing unit 30 generates a visible light image that is based on the reflected light of the visible light, a first fluorescent image that is based on the first fluorescence, and a second fluorescent image that is based on the second fluorescence on the basis of the first imaging signal and the second imaging signal output from the imaging device 206 and the imaging device 207.

First illumination light includes the visible light and the second excitation light. When the first illumination light is radiated on the subject 50, the imaging device 206 outputs a first signal as the first imaging signal. The first signal is an imaging signal that is based on reflected light of the visible light. The imaging device 207 outputs a second signal as the first imaging signal. The second signal is an imaging signal that is based on the second fluorescence. In other words, the first imaging signal includes the first signal and the second signal. When the first illumination light is radiated on the subject 50, the signal processing unit 30 generates the visible light image on the basis of the first signal and generates the second fluorescent image on the basis of the second signal.

The second illumination light includes the first excitation light and the second excitation light. When the second illumination light is radiated on the subject 50, the imaging device 206 outputs a third signal as the second imaging signal. The third signal is an imaging signal that is based on the first fluorescence. The imaging device 207 outputs a fourth signal as the second imaging signal. The fourth signal is an imaging signal that is based on the second fluorescence. In other words, the second imaging signal includes the third signal and the fourth signal. When the second illumination light is radiated on the subject 50, the signal processing unit 30 generates the first fluorescent image on the basis of the third signal and generates the second fluorescent image on the basis of the fourth signal.

The endoscope device 1a further includes a dichroic mirror 205 (light separation device). The dichroic mirror 205 separates the reflected light of the visible light and the second fluorescence from each other and separates the first fluorescence and the second fluorescence from each other. The reflected light of the visible light and the first fluorescence separated by the dichroic mirror 205 are incident to the imaging device 206. The second fluorescence separated by the dichroic mirror 205 is incident to the imaging device 207. When the first illumination light is radiated on the subject 50, the imaging device 206 outputs the first signal and the imaging device 207 outputs the second signal. When the second illumination light is radiated on the subject 50, the imaging device 206 outputs the third signal and the imaging device 207 outputs the fourth signal.

Regarding a detailed configuration of the endoscope device 1a, points different from the configuration shown in FIG. 1 will be described. In the endoscope device 1a, the scope unit 20 shown in FIG. 1 is changed to a scope unit 20a. The scope unit 20a includes a light guide 200, an illumination lens 201, an objective lens 202, an excitation wavelength blocking filter 203, the dichroic mirror 205, the imaging device 206, and the imaging device 207. The imaging device 206 and the imaging device 207 constitutes an imaging unit.

The dichroic mirror 205 is disposed on the optical path from the excitation wavelength blocking filter 203 to the imaging device 206 and the imaging device 207. Due to the spectral transmission characteristics of the excitation wavelength blocking filter 203, the reflected light of the visible light, the first fluorescence, and the second fluorescence are incident to the dichroic mirror 205. The imaging device 206 is disposed on the optical path of light transmitted through the dichroic mirror 205. The imaging device 207 is disposed on the optical path of light reflected by the dichroic mirror 205.

Figure 11:
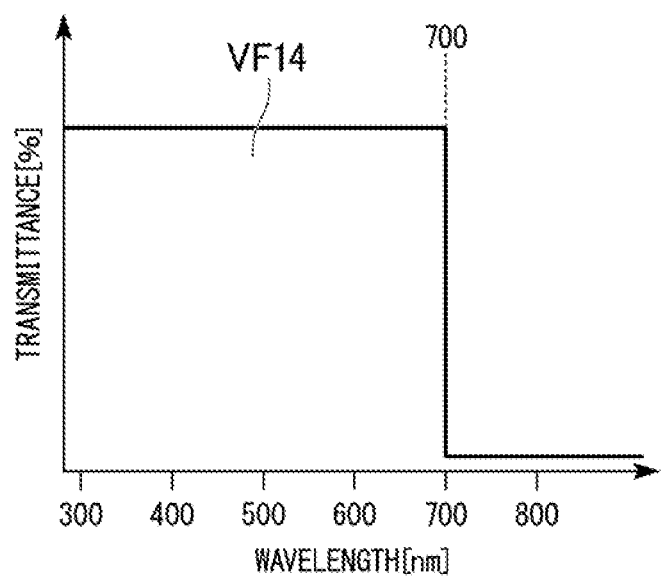
FIG. 11 is a graph showing spectral transmission characteristics of a dichroic mirror according to the modified example of the first embodiment of the present invention.

FIG. 11 shows spectral transmission characteristics of the dichroic mirror 205. In FIG. 11, the horizontal axis of the graph represents a wavelength and the vertical axis of the graph represents transmittance. As shown in FIG. 11, a transmission wavelength band of the dichroic mirror 205 includes a wavelength band VF14 of 700 nm or less. The wavelength band VF14 includes a wavelength band of 380 nm to 650 nm corresponding to the visible light and a wavelength band of 380 nm to 550 nm corresponding to the first fluorescence. The dichroic mirror 205 reflects light of a wavelength band other than the wavelength band VF14. A reflection wavelength band of the dichroic mirror 205 includes a wavelength band of 700 nm to 800 nm corresponding to the second fluorescence. Therefore, the dichroic mirror 205 transmits the reflected light of the visible light and the first fluorescence and reflects the second fluorescence.

When the first illumination light including the visible light and the second excitation light is radiated on the subject 50, the reflected light of the visible light and the second fluorescence are incident to the dichroic mirror 205. The dichroic mirror 205 transmits the reflected light of the visible light and reflects the second fluorescence. The reflected light of the visible light transmitted through the dichroic mirror 205 is incident to the imaging device 206. The second fluorescence reflected by the dichroic mirror 205 is incident to the imaging device 207. The imaging device 206 captures an image of the reflected light of the visible light and generates the first signal that is based on the reflected light of the visible light. The imaging device 207 captures an image of the second fluorescence and generates the second signal that is based on the second fluorescence. The first imaging signal including the first signal and the second signal is output to the signal processing unit 30.

When the second illumination light including the first excitation light and the second excitation light is radiated on the subject 50, the first fluorescence and the second fluorescence are incident to the dichroic mirror 205. The dichroic mirror 205 transmits the first fluorescence and reflects the second fluorescence. The first fluorescence transmitted through the dichroic mirror 205 is incident to the imaging device 206. The second fluorescence reflected by the dichroic mirror 205 is incident to the imaging device 207. The imaging device 206 captures an image of the first fluorescence and generates the third signal that is based on the first fluorescence. The imaging device 207 captures an image of the second fluorescence and generates the fourth signal that is based on the second fluorescence. The second imaging signal including the third signal and the fourth signal is output to the signal processing unit 30.

In terms of points other than the above, the configuration shown in FIG. 10 is similar to the configuration shown in FIG. 1.

The endoscope device 1a according to the modification example of the first embodiment can suppress reduction of the frame rate of the visible light image and can acquire the visible light image and the plural types of fluorescent images.

Second Embodiment

A second embodiment of the present invention will be described by using the endoscope device 1 shown in FIG. 1. In the second embodiment, a fluorescent agent of which the type is different from that of the fluorescent agent used in the first embodiment is used. In the second embodiment, a wavelength band of the visible light necessary for acquiring form information of an object for observation is different. If an image of light of a wavelength band having at least about 100 nm width out of a wavelength band of 400 nm to 700 nm is captured, the endoscope device 1 can acquire the form information of the object for observation.

In the second embodiment, a case where fluorescence emitted from a fluorescent substance metabolized from 5-aminolevulinic acid (ALA) and fluorescence emitted from indocyanine green (ICG) are detected will be described. 5-ALA is a useful agent for observation of cancer cells. ICG is a useful fluorescent agent for observation of blood vessels. Cancer cells need blood that carries nutrition and oxygen around them for their growth and proliferate new blood vessels (tumor blood vessels). Tumor blood vessels tend to be more bended or crooked compared to normal blood vessels. Tumor blood vessels have uneven diameters and run in a disorderly manner. Therefore, performance of diagnosis for cancer cells is improved by simultaneously performing observation of cancer cells and observation of blood vessels.

When 5-ALA is administered inside a living body, protoporphyrin IX (PpIX) metabolized from 5-ALA is accumulated in cancer cells in high concentration. PpIX is a fluorescent substance and emits strong fluorescence. It is possible to observe cancer cells by observing the fluorescence.

Figure 27:
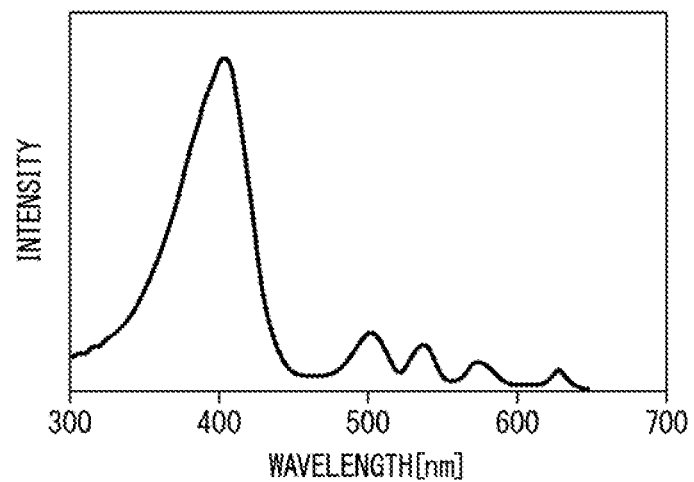
FIG. 27 is a graph showing excitation light absorption characteristics of PpIX.

FIG. 27 shows excitation light absorption characteristics of PpIX. In FIG. 27, the horizontal axis of the graph represents a wavelength and the vertical axis of the graph represents intensity.

As shown in FIG. 27, the wavelength of excitation light at which the intensity of fluorescence emitted from PpIX is highest is approximately 405 nm. Especially, PpIX emits strong fluorescence for excitation light having wavelengths of 370 nm to 450 nm.

Figure 28:
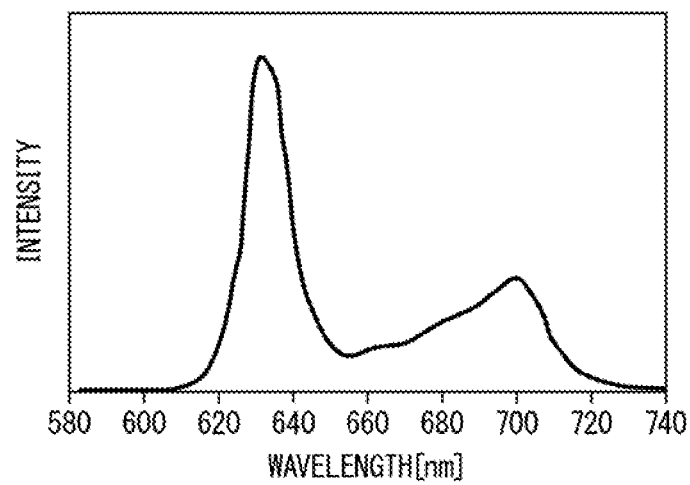
FIG. 28 is a graph showing fluorescence spectrum of PpIX.

FIG. 28 shows fluorescence spectrum of PpIX. In FIG. 28, the horizontal axis of the graph represents a wavelength and the vertical axis of the graph represents intensity.

PpIX emits fluorescence having wavelengths of 620 nm to 710 nm. The wavelength at which the intensity of fluorescence emitted from PpIX is highest is approximately 635 nm. In the second embodiment, light having wavelengths of 370 nm to 410 nm is used as light for exciting PpIX. Therefore, fluorescence emitted from PpIX can be detected by radiating excitation light having wavelengths of 370 nm to 410 nm inside a living body and detecting light having wavelengths of 620 nm to 710 nm.

Figure 29:
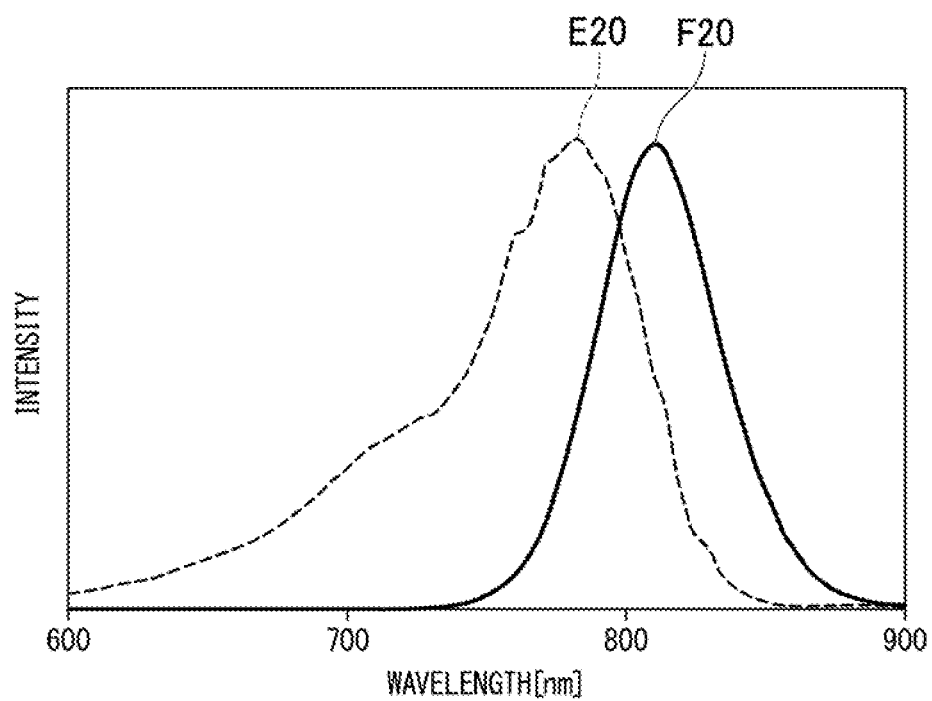
FIG. 29 is a graph showing excitation light absorption characteristics and fluorescence spectrum of ICG.
Figure 30:
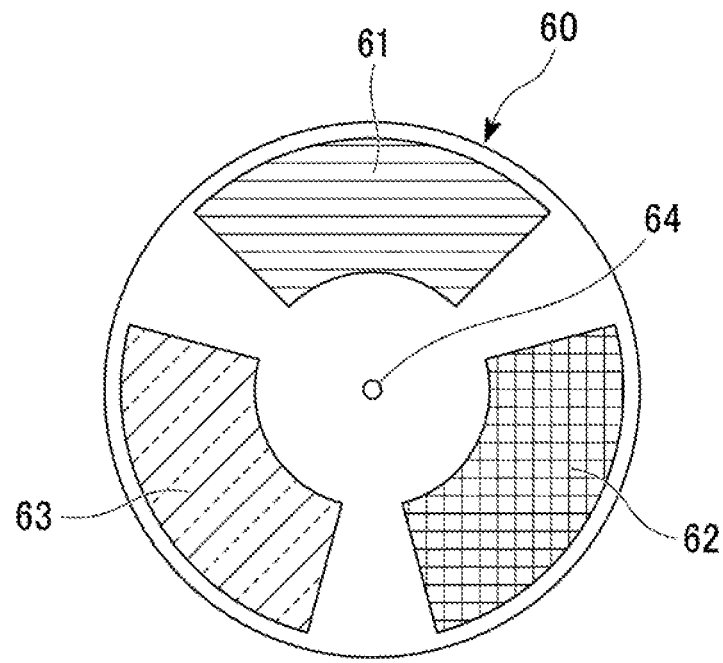
FIG. 30 is a schematic diagram showing a configuration of an excitation wavelength selection filter of related art.
Figure 31:
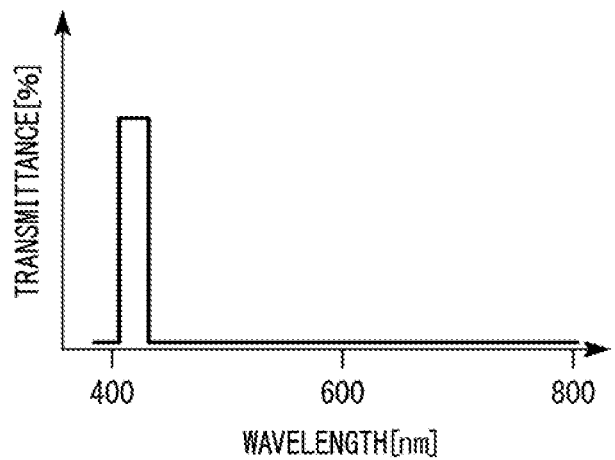
FIG. 31 is a graph showing spectral transmission characteristics of a first filter in an excitation wavelength selection filter of related art.
Figure 32:
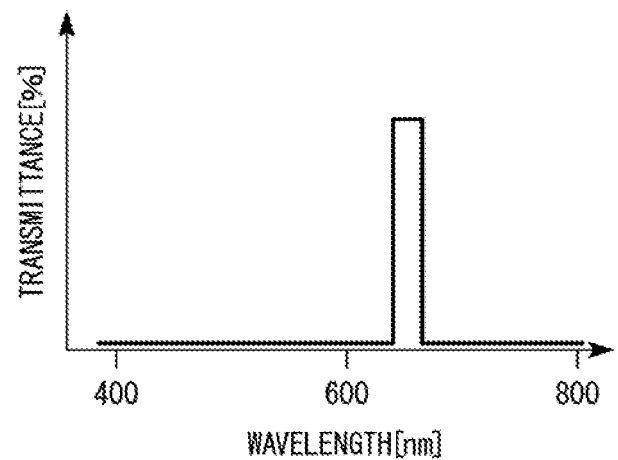
FIG. 32 is a graph showing spectral transmission characteristics of a second filter in the excitation wavelength selection filter of related art.
Figure 33:
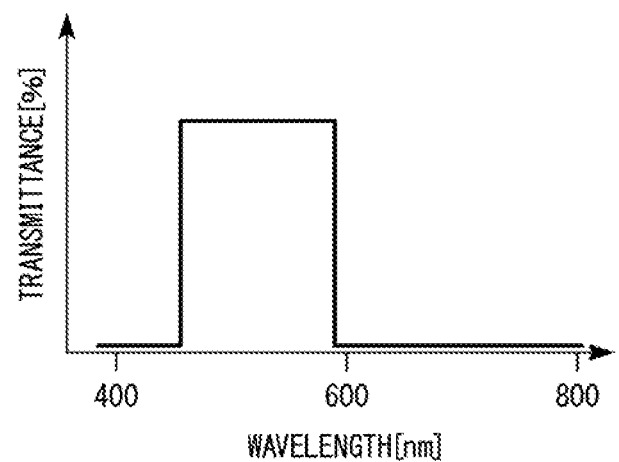
FIG. 33 is a graph showing spectral transmission characteristics of a third filter in the excitation wavelength selection filter of related art.
Figure 34:
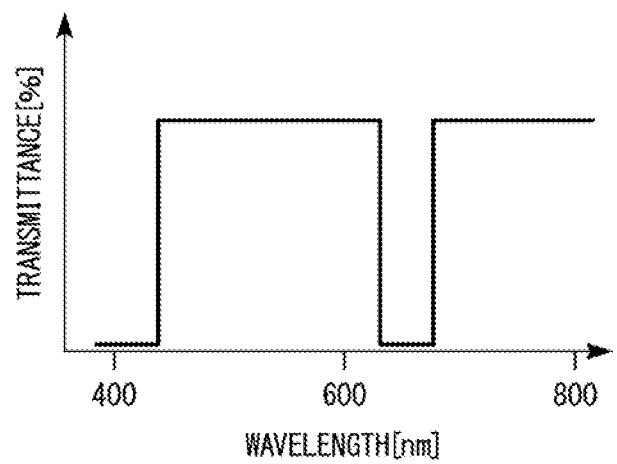
FIG. 34 is a graph showing spectral transmission characteristics of an excitation wavelength blocking filter of related art.
Figure 35:
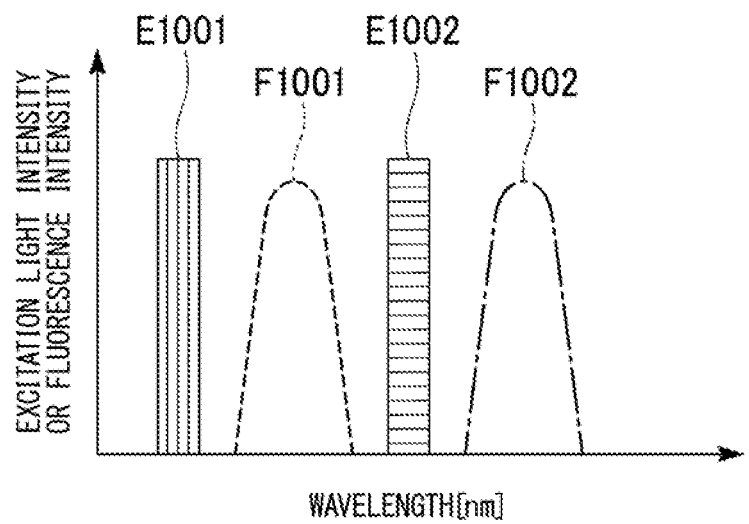
FIG. 35 is a graph showing spectral characteristics of excitation light and fluorescence of related art.

FIG. 29 shows excitation light absorption characteristics and fluorescence spectrum of ICG. In FIG. 29, the horizontal axis of the graph represents a wavelength and the vertical axis of the graph represents intensity. A line E20 represents excitation light absorption characteristics of ICG A line F20 represents fluorescence spectrum of ICG The wavelength of excitation light at which the intensity of fluorescence emitted from ICG is highest is 770 nm and the wavelength at which the intensity of fluorescence emitted from ICG is highest is 810 nm. Therefore, fluorescence emitted from ICG can be detected by radiating excitation light having wavelengths of 720 nm to 790 nm inside a living body and detecting light having wavelengths of 800 nm to 900 nm.

Regarding the configuration of the endoscope device 1, points different from the configuration in the first embodiment will mainly be described. In the second embodiment, a first fluorescent substance excited by the first excitation light is PpIX. In the second embodiment, a second fluorescent substance excited by the second excitation light is ICG.

Figure 12:
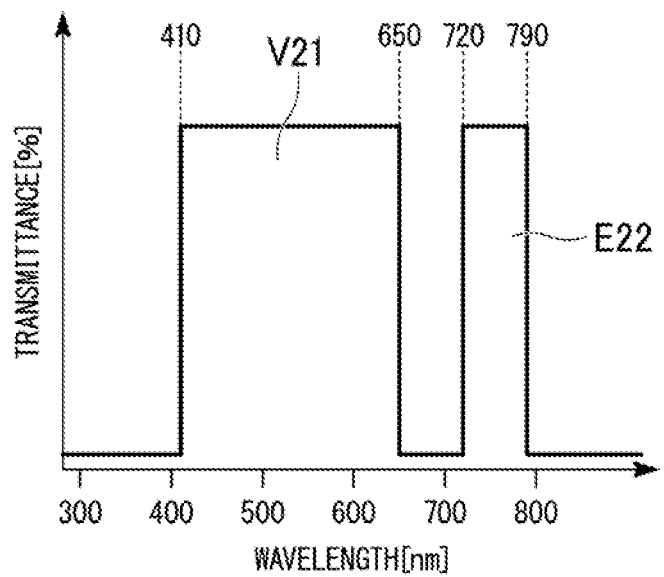
FIG. 12 is a graph showing spectral transmission characteristics of a first filter in an excitation wavelength selection filter according to a second embodiment of the present invention.

FIG. 12 shows spectral transmission characteristics of the first filter 1011 of the excitation wavelength selection filter 101. In FIG. 12, the horizontal axis of the graph represents a wavelength and the vertical axis of the graph represents transmittance. As shown in FIG. 12, a transmission wavelength band of the first filter 1011 includes a wavelength band V21 of 410 nm to 650 nm and a wavelength band E22 of 720 nm to 790 nm. The wavelength band V21 corresponds to the visible light. The wavelength band E22 corresponds to the second excitation light for exciting ICG The first filter 1011 blocks light of a wavelength band other than the wavelength band V21 and the wavelength band E22. Therefore, the first filter 1011 transmits only the visible light and the second excitation light.

Figure 13:
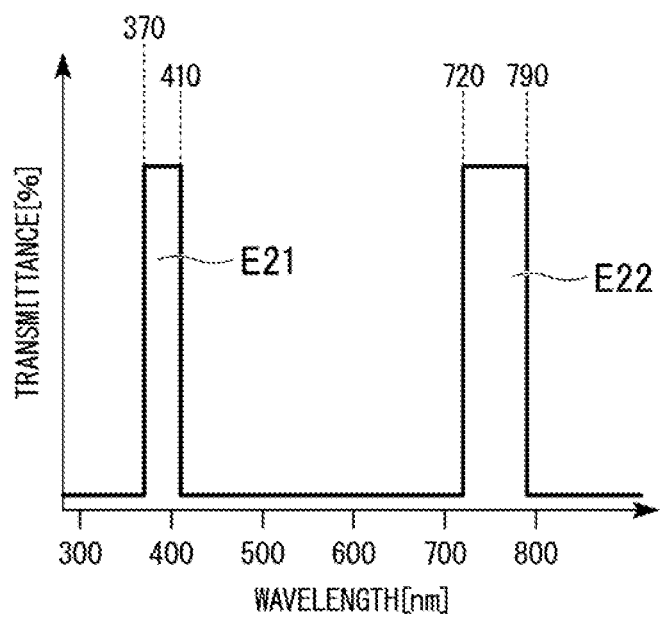
FIG. 13 is a graph showing spectral transmission characteristics of a second filter in an excitation wavelength selection filter according to the second embodiment of the present invention.

FIG. 13 shows spectral transmission characteristics of the second filter 1012 of the excitation wavelength selection filter 101. In FIG. 13, the horizontal axis of the graph represents a wavelength and the vertical axis of the graph represents transmittance. As shown in FIG. 13, a transmission wavelength band of the second filter 1012 includes a wavelength band E21 of 370 nm to 410 nm and a wavelength band E22 of 720 nm to 790 nm. The wavelength band E21 corresponds to the first excitation light for exciting PpIX. The second filter 1012 blocks light of a wavelength band other than the wavelength band E21 and the wavelength band E22. In other words, the second filter 1012 transmits only the first excitation light and the second excitation light.

Figure 14:
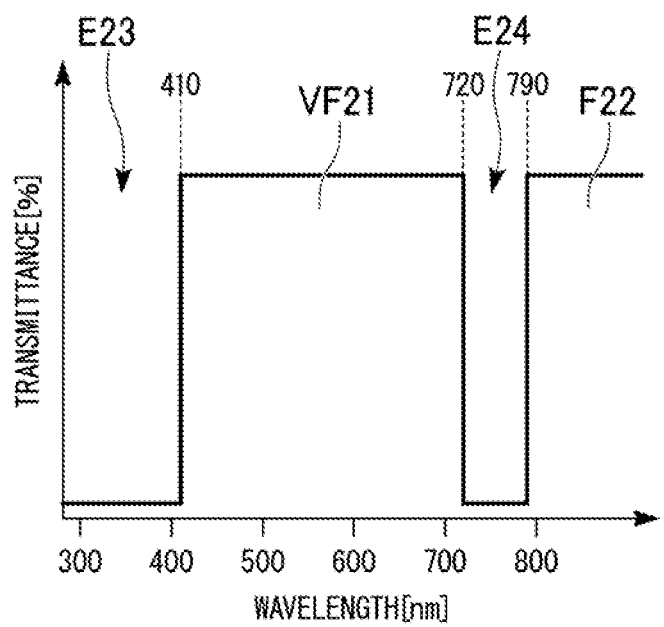
FIG. 14 is a graph showing spectral transmission characteristics of an excitation wavelength blocking filter according to the second embodiment of the present invention.

FIG. 14 shows spectral transmission characteristics of the excitation wavelength blocking filter 203. In FIG. 14, the horizontal axis of the graph represents a wavelength and the vertical axis of the graph represents transmittance. As shown in FIG. 14, a blocking wavelength band of the excitation wavelength blocking filter 203 includes a wavelength band E23 of 410 nm or less and a wavelength band E24 of 720 nm to 790 nm. The wavelength band E23 includes the wavelength band E21 of the first excitation light shown in FIG. 13. The wavelength band E24 includes the wavelength band E22 of the second excitation light shown in FIG. 13. Therefore, the excitation wavelength blocking filter 203 blocks reflected light of the first excitation light and reflected light of the second excitation light.

As shown in FIG. 14, a transmission wavelength band of the excitation wavelength blocking filter 203 includes a wavelength band VF21 of 410 nm to 720 nm and a wavelength band F22 of 790 nm or more. The wavelength band VF21 includes a wavelength band of 410 nm to 650 nm corresponding to the visible light and a wavelength band of 620 nm to 710 nm corresponding to the first fluorescence. The wavelength band F22 includes a wavelength band of 800 nm to 900 nm corresponding to the second fluorescence. Therefore, the excitation wavelength blocking filter 203 transmits reflected light of the visible light, the first fluorescence, and the second fluorescence.

As shown in FIG. 6, the imaging device 204 includes the first substrate 2040, the second substrate 2041, the color filter 2042, and the optical filter 2043. The color filter 2042 includes the red filter 2042R, the green filter 2042G, and the blue filter 2042B.

As shown by the line Lb1 in FIG. 26, the B pixel Pb1 has sensitivity in part of a wavelength band of 410 nm to 650 nm corresponding to the visible light, part of a wavelength band of 620 nm to 710 nm corresponding to the first fluorescence, and a wavelength band of 800 nm to 900 nm corresponding to the second fluorescence. In other words, the B pixel Pb1 detects the reflected light of the visible light, the first fluorescence, and the second fluorescence.

As shown by the line Lg1 in FIG. 26, the G pixel Pg1 has sensitivity in part of a wavelength band of 410 nm to 650 nm corresponding to the visible light, part of a wavelength band of 620 nm to 710 nm corresponding to the first fluorescence, and a wavelength band of 800 nm to 900 nm corresponding to the second fluorescence. In other words, the G pixel Pg1 detects the reflected light of the visible light, the first fluorescence, and the second fluorescence.

As shown by the line Lr1 in FIG. 26, the R pixel Pr1 has sensitivity in part of a wavelength band of 410 nm to 650 nm corresponding to the visible light, a wavelength band of 620 nm to 710 nm corresponding to the first fluorescence, and a wavelength band of 800 nm to 900 nm corresponding to the second fluorescence. In other words, the R pixel Pr1 detects the reflected light of the visible light, the first fluorescence, and the second fluorescence.

Figure 15:
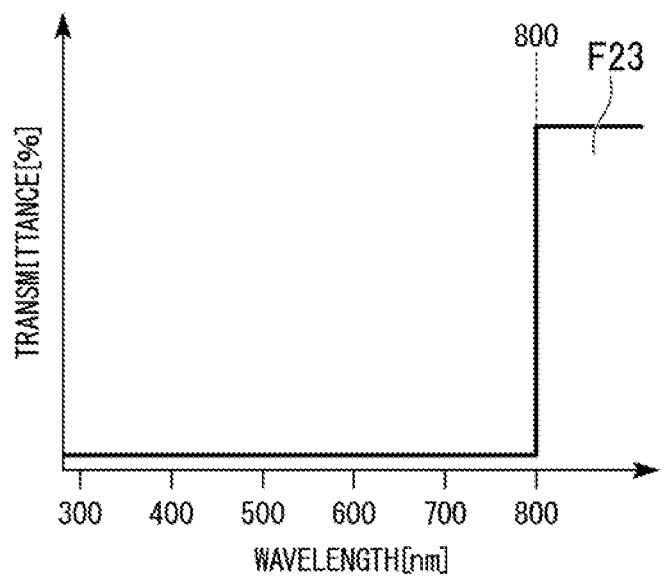
FIG. 15 is a graph showing spectral transmission characteristics of an optical filter according to the second embodiment of the present invention.

FIG. 15 shows spectral transmission characteristics of the optical filter 2043. In FIG. 15, the horizontal axis of the graph represents a wavelength and the vertical axis of the graph represents transmittance. As shown in FIG. 15, a transmission wavelength band of the optical filter 2043 includes a wavelength band F23 of 800 nm or more. The wavelength band F23 includes a wavelength band of 800 nm to 900 nm corresponding to the second fluorescence. The optical filter 2043 blocks light of a wavelength band other than the wavelength band F23. Therefore, the optical filter 2043 blocks the reflected light of the visible light and the first fluorescence and transmits the second fluorescence.

An operation of the endoscope device 1 will be described. When the excitation wavelength selection filter 101 rotates, the first illumination light transmitted through the first filter 1011 and the second illumination light transmitted through the second filter 1012 are sequentially radiated on the subject 50. The first illumination light includes the visible light and the second excitation light. The second illumination light includes the first excitation light and the second excitation light.

An operation of the endoscope device 1 when the first illumination light is radiated on the subject 50 will be described. Due to the spectral transmission characteristics of the first filter 1011 shown in FIG. 12, the visible light having wavelengths of 410 nm to 650 nm and the second excitation light having wavelengths of 720 nm to 790 nm are radiated on the subject 50. Reflected light of the visible light, reflected light of the second excitation light, and the second fluorescence having wavelengths of 800 nm to 900 nm are emitted from the subject 50.

The light emitted from the subject 50 is incident to the excitation wavelength blocking filter 203. The excitation wavelength blocking filter 203 blocks the reflected light of the second excitation light and transmits the reflected light of the visible light and the second fluorescence due to the spectral transmission characteristics shown in FIG. 14. The reflected light of the visible light and the second fluorescence transmitted through the excitation wavelength blocking filter 203 are incident to the imaging device 204.

The reflected light of the visible light and the second fluorescence are incident to the first photoelectric conversion element 2050 of each of the B pixel Pb1, the G pixel Pg1, and the R pixel Pr1 of the first substrate 2040. The second fluorescence is feeble enough to be ignored, compared to the reflected light of the visible light. For this reason, the plurality of first pixels 2040P of the first substrate 2040 output the first signal that is based on the reflected light of the visible light. The signal processing unit 30 generates the visible light image on the basis of the first signal.

Out of light incident to the imaging device 204, most of light having wavelengths of 500 nm or less is absorbed in the first substrate 2040 and only part of light having wavelengths of 500 nm or more is transmitted through the first substrate 2040. In other words, part of the reflected light of the visible light incident to the imaging device 204 and part of the second fluorescence incident to the imaging device 204 are transmitted through the first substrate 2040.

The light transmitted through the first substrate 2040 is incident to the optical filter 2043. The optical filter 2043 blocks the reflected light of the visible light transmitted through the first substrate 2040 and transmits the second fluorescence due to the spectral transmission characteristics shown in FIG. 15. The light transmitted through the optical filter 2043 is incident to the plurality of second photoelectric conversion elements 2051 of the second substrate 2041. The plurality of second pixels 2041P of the second substrate 2041 output the second signal that is based on the second fluorescence. The signal processing unit 30 generates the second fluorescent image on the basis of the second signal.

An operation of the endoscope device 1 when the second illumination light is radiated on the subject 50 will be described. Due to the spectral transmission characteristics of the second filter 1012 shown in FIG. 13, the first excitation light having wavelengths of 370 nm to 410 nm and the second excitation light having wavelengths of 720 nm to 790 nm are radiated on the subject 50. Reflected light of the first excitation light, reflected light of the second excitation light, the first fluorescence having wavelengths of 620 nm to 710 nm, and the second fluorescence having wavelengths of 800 nm to 900 nm are emitted from the subject 50.

The light emitted from the subject 50 is incident to the excitation wavelength blocking filter 203. The excitation wavelength blocking filter 203 blocks the reflected light of the first excitation light and the reflected light of the second excitation light and transmits the first fluorescence and the second fluorescence due to the spectral transmission characteristics shown in FIG. 14. The first fluorescence and the second fluorescence transmitted through the excitation wavelength blocking filter 203 are incident to the imaging device 204.

The first fluorescence and the second fluorescence are incident to the first photoelectric conversion element 2050 of each of the B pixel Pb1, the G pixel Pg1, and the R pixel Pr1 of the first substrate 2040. The plurality of first pixels 2040P of the first substrate 2040 output the third signal that is based on the first fluorescence and the second fluorescence.

Part of the first fluorescence incident to the imaging device 204 and part of the second fluorescence incident to the imaging device 204 are transmitted through the first substrate 2040. The light transmitted through the first substrate 2040 is incident to the optical filter 2043. The optical filter 2043 blocks the first fluorescence transmitted through the first substrate 2040 and transmits the second fluorescence due to the spectral transmission characteristics shown in FIG. 15. The light transmitted through the optical filter 2043 is incident to the plurality of second photoelectric conversion elements 2051 of the second substrate 2041. The plurality of second pixels 2041P of the second substrate 2041 output the fourth signal that is based on the second fluorescence. The signal processing unit 30 generates the second fluorescent image on the basis of the fourth signal. In addition, the signal processing unit 30 generates the first fluorescent image on the basis of the third signal and the fourth signal.

Here, in order for the first fluorescence and the second fluorescence to be incident to the first photoelectric conversion element 2050 of each pixel, it is necessary to separate the signal due to the first fluorescence and the signal due to the second fluorescence detected in the first photoelectric conversion element 2050 of each pixel from each other and to detect only the signal due to the first fluorescence. An example in which only the signal due to the first fluorescence is calculated will be described.

In the description below, $\alpha$ represents a rate at which the R pixel Pr1 of the first substrate 2040 absorbs the first fluorescence, $\beta$ represents a rate at which the R pixel Pr1 of the first substrate 2040 absorbs the second fluorescence, and $\gamma$ represents a rate at which the second pixel 2041P of the second substrate 2041 absorbs the second fluorescence. $\alpha$, $\beta$, and $\gamma$ can be calculated on the basis of the spectral sensitivity of the first substrate 2040 and the second substrate 2041. The ratio between $\beta$ and $\gamma$ is determined on the basis of the ratio between the spectral sensitivity of the R pixel Pr1 of the first substrate 2040 in the wavelength band of 800 nm to 900 nm corresponding to the second fluorescence and the spectral sensitivity of the second pixel 2041P of the second substrate 2041 in that wavelength band. $\alpha$, $\beta$, and $\gamma$ are parameters that are based on production conditions of the imaging device 204. For example, the production conditions include the thickness of each of the first substrate 2040 and the second substrate 2041 in the optical axis direction. Alternatively, the production conditions include the spectral transmission characteristics of the color filter 2042 and the optical filter 2043. α, β, and γ are real numbers 0 or more and 1 or less.

The R pixel Pr1 generates the third signal that is based on the first fluorescence and the second fluorescence. In the description below, the signal value of the third signal generated by the R pixel Pr1 is (αR+βIR). αR is the signal value that is based on the first fluorescence. βIR is the signal value that is based on the second fluorescence.

The second pixel 2041P generates the fourth signal that is based on the second fluorescence. In the description below, the signal value of the fourth signal generated by the second pixel 2041P is γIR. γIR is the signal value that is based on the second fluorescence. The fourth signal generated by the second pixel 2041P disposed at the position corresponding to the R pixel Pr1 is used. In other words, the fourth signal generated by the second pixel 2041P to which light transmitted through the R pixel Pr1 is incident is used.

The signal processing unit 30 multiplies the signal value of the fourth signal generated by the second pixel 2041P, that is, γIR by the ratio of β to γ, that is, (β/γ). In this way, the signal processing unit 30 can calculate the signal value βIR that is based on the second fluorescence detected by the first pixel 2040P. The signal processing unit 30 subtracts the signal value βIR calculated by using the above-described method from the signal value of the third signal (αR+βIR) generated by the R pixel Pr1. In this way, the signal processing unit 30 generates the signal that is based on only the first fluorescence. The signal value of this signal is αR.

The signal processing unit 30 may add the second signal that is based on the second fluorescence and the fourth signal that is based on the second fluorescence together. In this way, the SN ratio of the signal that is based on the second fluorescence is improved and the image quality of the second fluorescent image is improved.

Timings of an operation of the endoscope device 1 according to the second embodiment are similar to the timings shown in FIG. 9.

The light source unit 10 may include a plurality of light emitting devices capable of selectively emitting light of a wavelength band including the wavelength band of at least one of the visible light, the first excitation light, and the second excitation light similarly to the first embodiment. Each of the plurality of light emitting devices may be a light emitting diode.

The endoscope device 1 according to the second embodiment simultaneously captures an image of the reflected light of the visible light and the second fluorescence. Alternatively, the endoscope device 1 simultaneously captures an image of the first fluorescence and the second fluorescence. In this way, the interval of acquiring the visible light image is shortened. Therefore, the endoscope device 1 can suppress reduction of the frame rate of the visible light image and can acquire the visible light image and the plural types of fluorescent images.

The frame rate of the visible light image becomes faster compare to that of the related art. For this reason, the endoscope device 1 can suppress skipping of frames of the visible light image as much as possible. Consequently, moving images of the visible light image are easily watched and a user can easily understand the shape of an object for observation.

Modification Example of Second Embodiment

A modification example of the second embodiment of the present invention will be described by using the endoscope device 1*a* shown in FIG. 10. Regarding the configuration of the endoscope device 1*a*, points different from the configuration in the modification example of the first embodiment will mainly be described.

Figure 16:
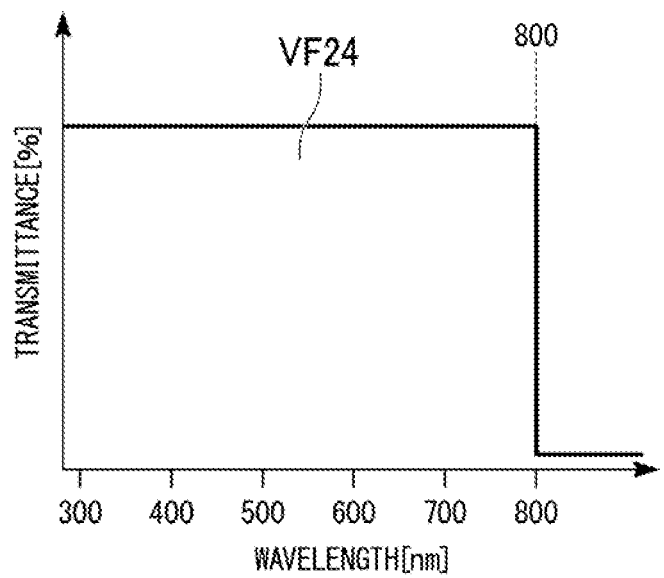
FIG. 16 is a graph showing spectral transmission characteristics of a dichroic mirror according to the modified example of the second embodiment of the present invention.

FIG. 16 shows spectral transmission characteristics of the dichroic mirror 205. In FIG. 16, the horizontal axis of the graph represents a wavelength and the vertical axis of the graph represents transmittance. As shown in FIG. 16, a transmission wavelength band of the dichroic mirror 205 includes a wavelength band VF24 of 800 nm or less. The wavelength band VF24 includes a wavelength band of 410 nm to 650 nm corresponding to the visible light and a wavelength band of 620 nm to 710 nm corresponding to the first fluorescence. The dichroic mirror 205 reflects light of a wavelength band other than the wavelength band VF24. A reflection wavelength band of the dichroic mirror 205 includes a wavelength band of 800 nm to 900 nm corresponding to the second fluorescence. Therefore, the dichroic mirror 205 transmits the reflected light of the visible light and the first fluorescence and reflects the second fluorescence.

The endoscope device 1*a* according to the modification example of the second embodiment can suppress reduction of the frame rate of the visible light image and can acquire the visible light image and the plural types of fluorescent images.

Third Embodiment

A third embodiment of the present invention will be described by using the endoscope device 1 shown in FIG. 1. The third embodiment is a modification example of the second embodiment.

In the third embodiment, the endoscope device 1 is capable of acquiring the visible light image at all times. In the third embodiment, a wavelength band of the visible light necessary for acquiring form information of an object for observation is narrower than the wavelength band of the visible light in the first embodiment and the wavelength band of the visible light in the second embodiment. The wavelength band of the visible light in the first embodiment is from 380 nm to 650 nm. The wavelength band of the visible light in the second embodiment is from 410 nm to 650 nm. The wavelength band of the visible light in the third embodiment is from 410 nm to 610 nm. If an image of light of a wavelength band having at least about 100 nm width out of a wavelength band of 400 nm to 700 nm is captured, the endoscope device 1 can acquire the form information of the object for observation.

In the second embodiment, in order to detect fluorescence emitted from PpIX, signal processing using a signal of the first pixel 2040P of the first substrate 2040 and a signal of the second pixel 2041P of the second substrate 2041 is performed. In the third embodiment, such signal processing is unnecessary.

Regarding the configuration of the endoscope device 1, points different from the configuration in the second embodiment will mainly be described. In the third embodiment, a first fluorescent substance excited by the first excitation light is PpIX. In the third embodiment, a second fluorescent substance excited by the second excitation light is ICG The light source unit 10 sequentially emits the first illumination light and the second illumination light. The first illumination light includes the first excitation light. The second illumination light includes the second excitation light. At least one of the first illumination light and the second illumination light includes the visible light. The imaging device 204 outputs the first imaging signal and the second imaging signal. The first imaging signal is based on the first fluorescence. The second imaging signal is based on the second fluorescence. At least one of the first imaging signal and the second imaging signal is further based on the reflected light of the visible light.

The light source 100 emits light of a wavelength band including at least a wavelength band of each of the visible light, the first excitation light, and the second excitation light. The first filter 1011 of the excitation wavelength selection filter 101 transmits the first excitation light. The second filter 1012 of the excitation wavelength selection filter 101 transmits the second excitation light. At least one of the first filter 1011 and the second filter 1012 transmits the visible light.

The first illumination light includes the visible light and the first excitation light. When the first illumination light is radiated on the subject 50, the imaging device 204 outputs a first signal and a second signal as the first imaging signal. The first signal is an imaging signal that is based on the reflected light of the visible light. The second signal is an imaging signal that is based on the first fluorescence. When the first illumination light is radiated on the subject 50, the signal processing unit 30 generates the visible light image on the basis of the first signal and generates the first fluorescent image on the basis of the second signal.

The second illumination light includes the visible light and the second excitation light. When the second illumination light is radiated on the subject 50, the imaging device 204 outputs a third signal and a fourth signal as the second imaging signal. The third signal is an imaging signal that is based on the visible light. The fourth signal is an imaging signal that is based on the second fluorescence. When the second illumination light is radiated on the subject 50, the signal processing unit 30 generates the visible light image on the basis of the third signal and generates the second fluorescent image on the basis of the fourth signal.

Figure 17:
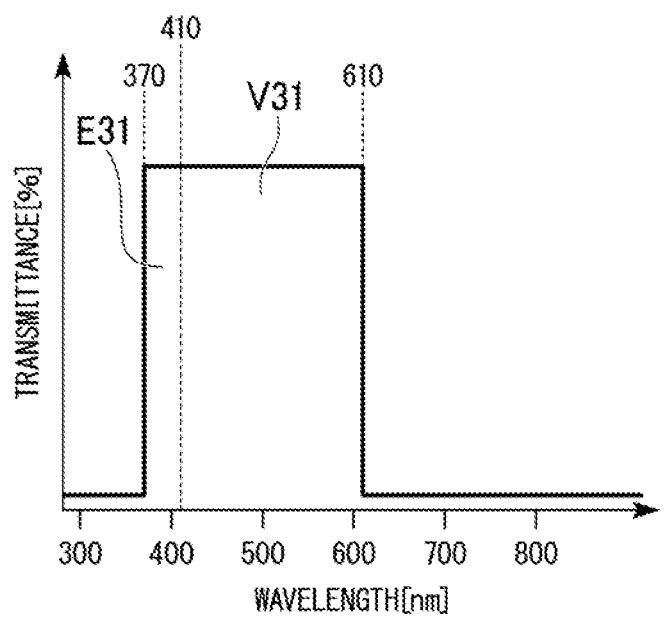
FIG. 17 is a graph showing spectral transmission characteristics of a first filter in an excitation wavelength selection filter according to a third embodiment of the present invention.

FIG. 17 shows spectral transmission characteristics of the first filter 1011 of the excitation wavelength selection filter 101. In FIG. 17, the horizontal axis of the graph represents a wavelength and the vertical axis of the graph represents transmittance. As shown in FIG. 17, a transmission wavelength band of the first filter 1011 includes a wavelength band E31 of 370 nm to 410 nm and a wavelength band V31 of 410 nm to 610 nm. The wavelength band E31 corresponds to the first excitation light for exciting PpIX. The wavelength band V31 corresponds to the visible light. The first filter 1011 blocks light of a wavelength band other than the wavelength band E31 and the wavelength band V31. Therefore, the first filter 1011 transmits only the visible light and the first excitation light.

Figure 18:
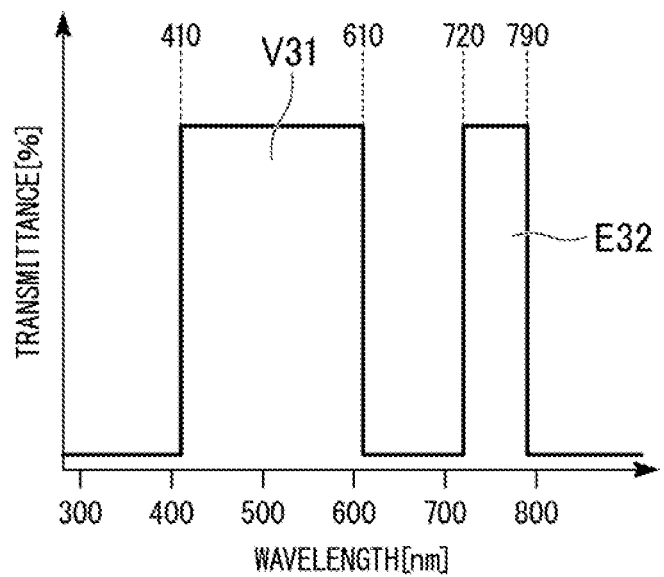
FIG. 18 is a graph showing spectral transmission characteristics of a second filter in an excitation wavelength selection filter according to the third embodiment of the present invention.

FIG. 18 shows spectral transmission characteristics of the second filter 1012 of the excitation wavelength selection filter 101. In FIG. 18, the horizontal axis of the graph represents a wavelength and the vertical axis of the graph represents transmittance. As shown in FIG. 18, a transmission wavelength band of the second filter 1012 includes a wavelength band V31 of 410 nm to 610 nm and a wavelength band E32 of 720 nm to 790 nm. The wavelength band V31 corresponds to the visible light. The wavelength band E32 corresponds to the second excitation light for exciting ICG The second filter 1012 blocks light of a wavelength band other than the wavelength band V31 and the wavelength band E32. In other words, the second filter 1012 transmits only the visible light and the second excitation light.

Figure 19:
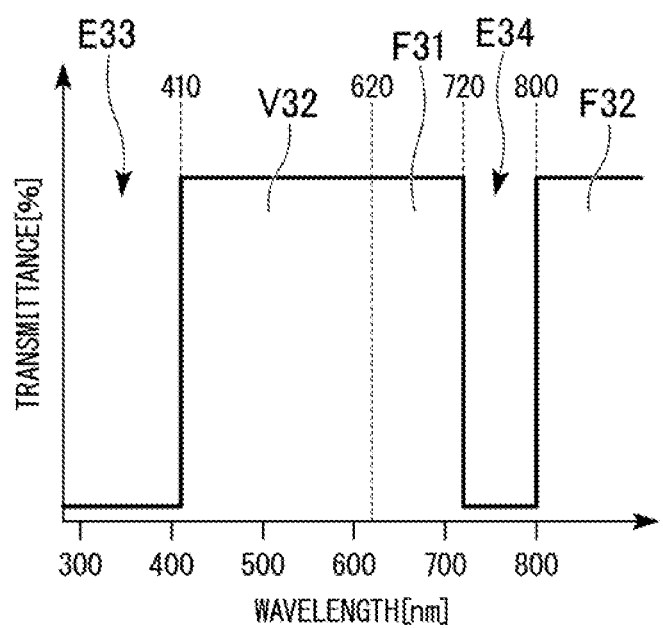
FIG. 19 is a graph showing spectral transmission characteristics of an excitation wavelength blocking filter according to the third embodiment of the present invention.

FIG. 19 shows spectral transmission characteristics of the excitation wavelength blocking filter 203. In FIG. 19, the horizontal axis of the graph represents a wavelength and the vertical axis of the graph represents transmittance. As shown in FIG. 19, a blocking wavelength band of the excitation wavelength blocking filter 203 includes a wavelength band E33 of 410 nm or less and a wavelength band E34 of 720 nm to 790 nm. The wavelength band E33 includes the wavelength band E31 of the first excitation light shown in FIG. 17. The wavelength band E34 includes the wavelength band E32 of the second excitation light shown in FIG. 18. Therefore, the excitation wavelength blocking filter 203 blocks reflected light of the first excitation light and reflected light of the second excitation light.

As shown in FIG. 19, a transmission wavelength band of the excitation wavelength blocking filter 203 includes a wavelength band V32 of 410 nm to 620 nm, a wavelength band F31 of 620 nm to 720 nm, and a wavelength band F32 of 800 nm or more. The wavelength band V31 includes a wavelength band of 410 nm to 610 nm corresponding to the visible light. The wavelength band F31 includes a wavelength band of 620 nm to 710 nm corresponding to the first fluorescence. The wavelength band F32 includes a wavelength band of 800 nm to 900 nm corresponding to the second fluorescence. Therefore, the excitation wavelength blocking filter 203 transmits reflected light of the visible light, the first fluorescence, and the second fluorescence.

As shown in FIG. 6, the imaging device 204 includes the first substrate 2040, the second substrate 2041 stacked on the first substrate 2040, and the optical filter 2043. As shown in FIG. 7, the first substrate 2040 includes the plurality of first pixels 2040P disposed two-dimensionally. The plurality of first pixels 2040P of the first substrate 2040 output the first signal and the third signal. As shown in FIG. 7, the second substrate 2041 includes the plurality of second pixels 2041P disposed two-dimensionally. The plurality of second pixels 2041P of the second substrate 2041 output the second signal and the fourth signal.

When the first illumination light is radiated on the subject 50, the imaging device 204 outputs the first signal and the second signal. When the second illumination light is radiated on the subject 50, the imaging device 204 outputs the third signal and the fourth signal. The optical filter 2043 is disposed between the first substrate 2040 and the second substrate 2041. The optical filter 2043 has an optical characteristic of blocking a wavelength band of the visible light and has an optical characteristic of transmitting a wavelength band of the first fluorescence and a wavelength band of the second fluorescence.

As shown in FIG. 6, the imaging device 204 further includes the color filter 2042. The color filter 2042 includes the red filter 2042R, the green filter 2042G, and the blue filter 2042B.

Figure 20:
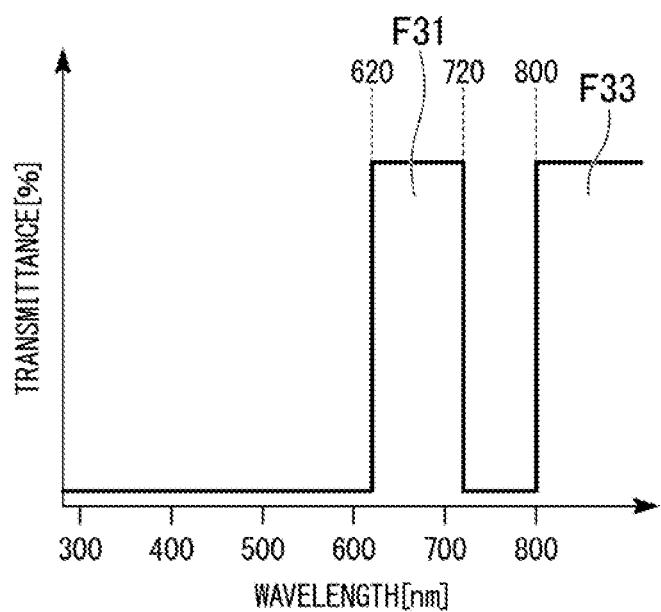
FIG. 20 is a graph showing spectral transmission characteristics of an optical filter according to the third embodiment of the present invention.

FIG. 20 shows spectral transmission characteristics of the optical filter 2043. In FIG. 20, the horizontal axis of the graph represents a wavelength and the vertical axis of the graph represents transmittance. As shown in FIG. 20, a transmission wavelength band of the optical filter 2043 includes a wavelength band F31 of 620 nm to 720 nm and a wavelength band F33 of 800 nm or more. The wavelength band F31 includes a wavelength band of 620 nm to 710 nm corresponding to the first fluorescence. The wavelength band F33 includes a wavelength band of 800 nm to 900 nm corresponding to the second fluorescence. The optical filter 2043 blocks light of a wavelength band other than the wavelength band F31 and the wavelength band F33. Therefore, the optical filter 2043 blocks the reflected light of the visible light and transmits the first fluorescence and the second fluorescence.

An operation of the endoscope device 1 will be described. When the excitation wavelength selection filter 101 rotates, the first illumination light transmitted through the first filter 1011 and the second illumination light transmitted through the second filter 1012 are sequentially radiated on the subject 50. The first illumination light includes the visible light and the first excitation light. The second illumination light includes the visible light and the second excitation light.

An operation of the endoscope device 1 when the first illumination light is radiated on the subject 50 will be described. Due to the spectral transmission characteristics of the first filter 1011 shown in FIG. 17, the visible light having wavelengths of 410 nm to 610 nm and the first excitation light having wavelengths of 370 nm to 410 nm are radiated on the subject 50. Reflected light of the visible light, reflected light of the first excitation light, and the first fluorescence having wavelengths of 620 nm to 710 nm are emitted from the subject 50.

The light emitted from the subject 50 is incident to the excitation wavelength blocking filter 203. The excitation wavelength blocking filter 203 blocks the reflected light of the first excitation light and transmits the reflected light of the visible light and the first fluorescence due to the spectral transmission characteristics shown in FIG. 19. The reflected light of the visible light and the first fluorescence transmitted through the excitation wavelength blocking filter 203 are incident to the imaging device 204.

The reflected light of the visible light and the first fluorescence are incident to the first photoelectric conversion element 2050 of each of the B pixel Pb1, the G pixel Pg1, and the R pixel Pr1 of the first substrate 2040. The first fluorescence is feeble enough to be ignored, compared to the reflected light of the visible light. For this reason, the plurality of first pixels 2040P of the first substrate 2040 output the first signal that is based on the reflected light of the visible light. The signal processing unit 30 generates the visible light image on the basis of the first signal.

Out of light incident to the imaging device 204, most of light having wavelengths of 600 nm or less is absorbed in the first substrate 2040 and only part of light having wavelengths of 600 nm or more is transmitted through the first substrate 2040. Out of light incident to the imaging device 204, part of light having wavelengths of 600 nm or more is not absorbed in the first substrate 2040 and is transmitted through the first substrate 2040. In other words, part of the reflected light of the visible light incident to the imaging device 204 and part of the first fluorescence incident to the imaging device 204 are transmitted through the first substrate 2040.

The light transmitted through the first substrate 2040 is incident to the optical filter 2043. The optical filter 2043 blocks the reflected light of the visible light transmitted through the first substrate 2040 and transmits the first fluorescence due to the spectral transmission characteristics shown in FIG. 20. The light transmitted through the optical filter 2043 is incident to the plurality of second photoelectric conversion elements 2051 of the second substrate 2041. The plurality of second pixels 2041P of the second substrate 2041 output the second signal that is based on the first fluorescence. The signal processing unit 30 generates the first fluorescent image on the basis of the second signal.

An operation of the endoscope device 1 when the second illumination light is radiated on the subject 50 will be described. Due to the spectral transmission characteristics of the second filter 1012 shown in FIG. 18, the visible light having wavelengths of 410 nm to 610 nm and the second excitation light having wavelengths of 720 nm to 790 nm are radiated on the subject 50. Reflected light of the visible light, reflected light of the second excitation light, and the second fluorescence having wavelengths of 800 nm to 900 nm are emitted from the subject 50.

The light emitted from the subject 50 is incident to the excitation wavelength blocking filter 203. The excitation wavelength blocking filter 203 blocks the reflected light of the second excitation light and transmits the reflected light of the visible light and the second fluorescence due to the spectral transmission characteristics shown in FIG. 19. The reflected light of the visible light and the second fluorescence transmitted through the excitation wavelength blocking filter 203 are incident to the imaging device 204.

The reflected light of the visible light and the second fluorescence are incident to the first photoelectric conversion element 2050 of each of the B pixel Pb1, the G pixel Pg1, and the R pixel Pr1 of the first substrate 2040. The second fluorescence is feeble enough to be ignored, compared to the reflected light of the visible light. For this reason, the plurality of first pixels 2040P of the first substrate 2040 output the third signal that is based on the reflected light of the visible light. The signal processing unit 30 generates the visible light image on the basis of the third signal.

Part of the reflected light of the visible light incident to the imaging device 204 and part of the second fluorescence incident to the imaging device 204 are transmitted through the first substrate 2040. The light transmitted through the first substrate 2040 is incident to the optical filter 2043. The optical filter 2043 blocks the reflected light of the visible light transmitted through the first substrate 2040 and transmits the second fluorescence due to the spectral transmission characteristics shown in FIG. 20. The light transmitted through the optical filter 2043 is incident to the plurality of second photoelectric conversion elements 2051 of the second substrate 2041. The plurality of second pixels 2041P of the second substrate 2041 output the fourth signal that is based on the second fluorescence. The signal processing unit 30 generates the second fluorescent image on the basis of the fourth signal.

Figure 21:
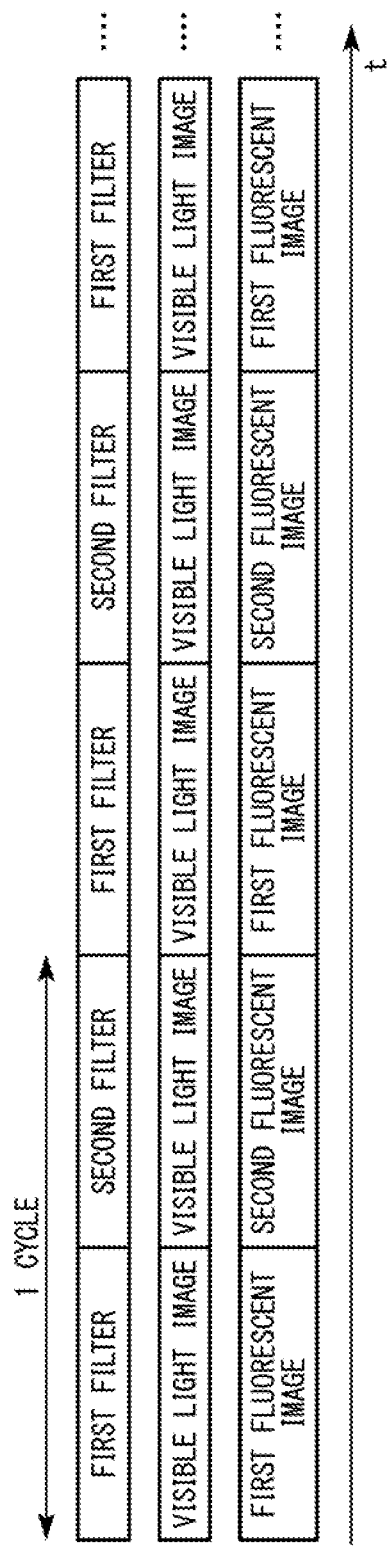
FIG. 21 is a timing chart showing an operation of an endoscope device according to the third embodiment of the present invention.

FIG. 21 is a timing chart showing the operation of the endoscope device 1. In FIG. 21, filter types of the excitation wavelength selection filter 101 disposed on the optical path are shown. In addition, in FIG. 21, an image that is based on the signal acquired in the first substrate 2040 and an image that is based on the signal acquired in the second substrate 2041 are shown. In FIG. 21, time passes in the right direction.

An operation in one cycle is repeated. In the first half period of the cycle, the first filter 1011 is disposed on the optical path. The first filter 1011 transmits the visible light and the first excitation light out of light emitted from the light source 100. The first illumination light including the visible light and the first excitation light is radiated on the subject 50. Reflected light of the visible light, reflected light of the first excitation light, and the first fluorescence are emitted from the subject 50 and incident to the imaging device 204. The reflected light of the visible light is detected in the first substrate 2040 and the first fluorescence is detected in the second substrate 2041. Consequently, the visible light image and the first fluorescent image are generated.

In the second half period of the cycle, the second filter 1012 is disposed on the optical path. The second filter 1012 transmits the visible light and the second excitation light out of light emitted from the light source 100. Reflected light of the visible light, reflected light of the second excitation light, and the second fluorescence are emitted from the subject 50 and incident to the imaging device 204. The reflected light of the visible light is detected in the first substrate 2040 and the second fluorescence is detected in the second substrate 2041. Consequently, the visible light image and the second fluorescent image are generated.

In the operation shown in FIG. 21, the reflected light of the visible light is detected in the first half period and the second half period of one cycle. The reflected light of the visible light may be detected in only the first half period or the second half period of one cycle.

The light source unit 10 may include a plurality of light emitting devices capable of selectively emitting light of a wavelength band including the wavelength band of at least one of the visible light, the first excitation light, and the second excitation light similarly to the first embodiment. For example, in a first period, at least one of the plurality of light emitting devices emits the visible light and the first excitation light. In a second period, at least one of the plurality of light emitting devices emits the visible light and the second excitation light. Each of the plurality of light emitting devices may be a light emitting diode.

The endoscope device 1 according to the third embodiment simultaneously captures an image of the reflected light of the visible light and the first fluorescence. Alternatively, the endoscope device 1 simultaneously captures an image of the reflected light of the visible light and the second fluorescence. In this way, the interval of acquiring the visible light image is shortened. Therefore, the endoscope device 1 can suppress reduction of the frame rate of the visible light image and can acquire the visible light image and the plural types of fluorescent images.

The frame rate of the visible light image becomes faster compare to that of the related art. For this reason, the endoscope device 1 can suppress skipping of frames of the visible light image as much as possible. Consequently, moving images of the visible light image are easily watched and a user can easily understand the shape of an object for observation.

Modification Example of Third Embodiment

A modification example of the third embodiment of the present invention will be described by using the endoscope device 1a shown in FIG. 10. Regarding the configuration of the endoscope device 1a, points different from the configuration in the modification example of the second embodiment will mainly be described.

The imaging device 206 captures an image of the visible light reflected by a subject 50. The imaging device 207 captures an image of first fluorescence excited by the first excitation light and emitted from the subject 50 and second fluorescence excited by the second excitation light and emitted from the subject 50. The imaging device 206 and the imaging device 207 output a first imaging signal and a second imaging signal. The excitation wavelength blocking filter 203 has a characteristic of blocking a wavelength band of the first excitation light and a wavelength band of the second excitation light and a characteristic of transmitting a wavelength band of the visible light, a wavelength band of the first fluorescence, and a wavelength band of the second fluorescence. The signal processing unit 30 generates a visible light image that is based on the visible light, a first fluorescent image that is based on the first fluorescence, and a second fluorescent image that is based on the second fluorescence on the basis of the first imaging signal and the second imaging signal output from the imaging device 206 and the imaging device 207.

First illumination light includes the visible light and the first excitation light. When the first illumination light is radiated on the subject 50, the imaging device 206 outputs a first signal as the first imaging signal. The first signal is an imaging signal that is based on reflected light of the visible light. The imaging device 207 outputs a second signal as the first imaging signal. The second signal is an imaging signal that is based on the first fluorescence. When the first illumination light is radiated on the subject 50, the signal processing unit 30 generates the visible light image on the basis of the first signal and generates the first fluorescent image on the basis of the second signal.

The second illumination light includes the visible light and the second excitation light. When the second illumination light is radiated on the subject 50, the imaging device 206 outputs a third signal as the second imaging signal. The third signal is an imaging signal that is based on the visible light. The imaging device 207 outputs a fourth signal as the second imaging signal. The fourth signal is an imaging signal that is based on the second fluorescence. When the second illumination light is radiated on the subject 50, the signal processing unit 30 generates the visible light image on the basis of the third signal and generates the second fluorescent image on the basis of the fourth signal.

The dichroic mirror 205 separates the reflected light of the visible light and the first fluorescence from each other when the first illumination light is radiated and separates the reflected light of the visible light and the second fluorescence from each other when the second illumination light is radiated. The reflected light of the visible light separated by the dichroic mirror 205 is incident to the imaging device 206. The first fluorescence and the second fluorescence separated by the dichroic mirror 205 are incident to the imaging device 207. When the first illumination light is radiated on the subject 50, the imaging device 206 outputs the first signal and the imaging device 207 outputs the second signal. When the second illumination light is radiated on the subject 50, the imaging device 206 outputs the third signal and the imaging device 207 outputs the fourth signal.

Figure 22:
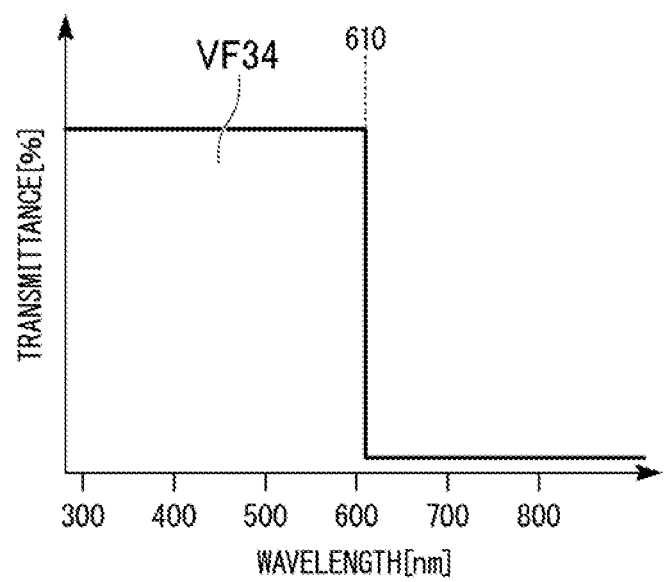
FIG. 22 is a graph showing spectral transmission characteristics of a dichroic mirror according to the modified example of the third embodiment of the present invention.

FIG. 22 shows spectral transmission characteristics of the dichroic mirror 205. In FIG. 22, the horizontal axis of the graph represents a wavelength and the vertical axis of the graph represents transmittance. As shown in FIG. 22, a transmission wavelength band of the dichroic mirror 205 includes a wavelength band VF34 of 610 nm or less. The wavelength band VF34 includes a wavelength band of 410 nm to 610 nm corresponding to the visible light. The dichroic mirror 205 reflects light of a wavelength band other than the wavelength band VF34. A reflection wavelength band of the dichroic mirror 205 includes a wavelength band of 620 nm to 710 nm corresponding to the first fluorescence and a wavelength band of 800 nm to 900 nm corresponding to the second fluorescence. Therefore, the dichroic mirror 205 transmits the reflected light of the visible light and reflects the first fluorescence and the second fluorescence.

When the first illumination light including the visible light and the first excitation light is radiated on the subject 50, the reflected light of the visible light and the first fluorescence are incident to the dichroic mirror 205. The dichroic mirror 205 transmits the reflected light of the visible light and reflects the first fluorescence. The reflected light of the visible light transmitted through the dichroic mirror 205 is incident to the imaging device 206. The first fluorescence reflected by the dichroic mirror 205 is incident to the imaging device 207. The imaging device 206 captures an image of the reflected light of the visible light and generates the first signal that is based on the reflected light of the visible light. The imaging device 207 captures an image of the first fluorescence and generates the second signal that is based on the first fluorescence. The first imaging signal including the first signal and the second signal is output to the signal processing unit 30.

When the second illumination light including the visible light and the second excitation light is radiated on the subject 50, the reflected light of the visible light and the second fluorescence are incident to the dichroic mirror 205. The dichroic mirror 205 transmits the reflected light of the visible light and reflects the second fluorescence. The reflected light of the visible light transmitted through the dichroic mirror 205 is incident to the imaging device 206. The second fluorescence reflected by the dichroic mirror 205 is incident to the imaging device 207. The imaging device 206 captures an image of the reflected light of the visible light and generates the third signal that is based on the reflected light of the visible light. The imaging device 207 captures an image of the second fluorescence and generates the fourth signal that is based on the second fluorescence. The second imaging signal including the third signal and the fourth signal is output to the signal processing unit 30.

The endoscope device 1a according to the modification example of the third embodiment can suppress reduction of the frame rate of the visible light image and can acquire the visible light image and the plural types of fluorescent images.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscope device comprising:
a light source unit configured to sequentially emit first illumination light and second illumination light, the first illumination light including visible light, the second illumination light including first excitation light for exciting a first fluorescent substance existing inside an object for observation, at least the second illumination light out of the first illumination light and the second illumination light including second excitation light for exciting a second fluorescent substance existing inside the object;
an imaging unit configured to receive reflected light that is the visible light reflected by the object, first fluorescence excited by the first excitation light and emitted from the object, and second fluorescence excited by the second excitation light and emitted from the object and configured to output a first imaging signal and a second imaging signal, the first imaging signal being generated on the basis of the reflected light, the second imaging signal being generated on the basis of the first fluorescence, at least the second imaging signal out of the first imaging signal and the second imaging signal being further generated on the basis of the second fluorescence;
an excitation wavelength blocking filter disposed on an optical path from the object to the imaging unit and having a characteristic of blocking a wavelength band of the first excitation light and a wavelength band of the second excitation light and a characteristic of transmitting a wavelength band of the visible light, a wavelength band of the first fluorescence, and a wavelength band of the second fluorescence; and
a signal processing unit configured to generate
a visible light image that is based on the reflected light,
a first fluorescent image that is based on the first fluorescence, and
a second fluorescent image that is based on the second fluorescence;
wherein the signal processing unit generates the images on the basis of the first imaging signal and the second imaging signal output from the imaging unit,
the first illumination light includes the visible light and the second excitation light,
the imaging unit is configured to output a first signal and a second signal as the first imaging signal when the first illumination light is radiated on the object, the first signal being generated on the basis of the reflected light, the second signal being generated on the basis of the second fluorescence,
the signal processing unit is configured to generate the visible light image on the basis of the first signal and generate the second fluorescent image on the basis of the second signal when the first illumination light is radiated on the object,
the second illumination light includes the first excitation light and the second excitation light,
the imaging unit is configured to output a third signal and a fourth signal as the second imaging signal when the second illumination light is radiated on the object, the third signal being generated on the basis of the first fluorescence and the second fluorescence, the fourth signal being generated on the basis of the second fluorescence,
the imaging unit includes:
a first imaging region configured to output the first signal and the third signal, and
a second imaging region configured to output the second signal and the fourth signal, and
the signal processing unit is configured to generate the first fluorescent image on the basis of the third signal and the fourth signal and generate the second fluorescent image on the basis of the fourth signal when the second illumination light is radiated on the object.

2. The endoscope device according to claim 1,
wherein the light source unit includes:
a light source configured to emit light of a wavelength band including at least the wavelength band of each of the visible light, the first excitation light, and the second excitation light; and
a rotation filter disposed on an optical path of light emitted from the light source and including a first filter and a second filter disposed in a circumferential direction thereof,
the first filter is configured to transmit the visible light and the second excitation light,
the second filter is configured to transmit the first excitation light and the second excitation light.

3. The endoscope device according to claim 1,
wherein the imaging unit includes
a first substrate as the first imaging region,
a second substrate stacked on the first substrate as the second imaging region, and
an optical filter, the first substrate includes a plurality of first pixels disposed two-dimensionally and configured to output the first signal and the third signal, the second substrate includes a plurality of second pixels disposed two-dimensionally and configured to output the second signal and the fourth signal, the imaging unit is configured to output the first signal and the second signal when the first illumination light is radiated on the object, the imaging unit is configured to output the third signal and the fourth signal when the second illumination light is radiated on the object, the optical filter is disposed between the first substrate and the second substrate, and the optical filter has an optical characteristic of blocking a wavelength band of the visible light and a wavelength band of the first fluorescence and an optical characteristic of transmitting a wavelength band of the second fluorescence.

4. The endoscope device according to claim 1, wherein the first illumination light includes the visible light and the second excitation light, the imaging unit is configured to output a first signal and a second signal as the first imaging signal when the first illumination light is radiated on the object, the first signal being generated on the basis of the reflected light, the second signal being generated on the basis of the second fluorescence, the signal processing unit is configured to generate the visible light image on the basis of the first signal and generate the second fluorescent image on the basis of the second signal when the first illumination light is radiated on the object, the second illumination light includes the first excitation light and the second excitation light, the imaging unit is configured to output a third signal and a fourth signal as the second imaging signal when the second illumination light is radiated on the object, the third signal being generated on the basis of the first fluorescence, the fourth signal being generated on the basis of the second fluorescence, and the signal processing unit is configured to generate the first fluorescent image on the basis of the third signal and generate the second fluorescent image on the basis of the fourth signal when the second illumination light is radiated on the object.

5. The endoscope device according to claim 4, further comprising a light separation device configured to separate the reflected light and the second fluorescence from each other and separate the first fluorescence and the second fluorescence from each other, wherein the imaging unit includes
a first imaging device to which the reflected light and the first fluorescence separated by the light separation device are incident, and
a second imaging device to which the second fluorescence separated by the light separation device is incident, the first imaging device is configured to output the first signal and the second imaging device is configured to output the second signal when the first illumination light is radiated on the object, and the first imaging device is configured to output the third signal and the second imaging device is configured to output the fourth signal when the second illumination light is radiated on the object.

6. The endoscope device according to claim 1, wherein the light source unit includes a plurality of light emitting devices capable of selectively emitting light of a wavelength band including the wavelength band of at least one of the visible light, the first excitation light, and the second excitation light.

7. The endoscope device according to claim 6, wherein the light emitting device included in the plurality of light emitting devices is a light emitting diode.

8. The endoscope device according to claim 1, wherein the first fluorescent substance is collagen and the second fluorescent substance is Alexa 680.

9. The endoscope device according to claim 1, wherein the first fluorescent substance is protoporphyrin IX and the second fluorescent substance is indocyanine green.

10. The endoscope device according to claim 1, wherein the signal processing unit is configured to generate a display image including the visible light image and at least one of the first fluorescent image and the second fluorescent image such that the visible light image and at least one of the first fluorescent image and the second fluorescent image are separated from each other in the display image.

11. The endoscope device according to claim 1, wherein the signal processing unit is configured to generate a display image including the visible light image and at least one of the first fluorescent image and the second fluorescent image such that at least part of the visible light image and at least part of at least one of the first fluorescent image and the second fluorescent image overlap each other in the display image.

* * * * *